United States Patent
Arden et al.

(10) Patent No.: US 10,342,526 B2
(45) Date of Patent: Jul. 9, 2019

(54) AIRWAY ASSIST DEVICE AND METHOD

(71) Applicant: Richard L. Arden, Farmington Hills, MI (US)

(72) Inventors: Richard L. Arden, Farmington Hills, MI (US); John F. Goodman, Ann Arbor, MI (US); Ryan Goosen, Caledonia, MI (US)

(73) Assignee: Richard L. Arden, Farmington Hills, MI (US)

( * ) Notice: Subject to any disclaimer, the term of this patent is extended or adjusted under 35 U.S.C. 154(b) by 601 days.

(21) Appl. No.: 15/200,463

(22) Filed: Jul. 1, 2016

(65) Prior Publication Data

US 2017/0000641 A1    Jan. 5, 2017

Related U.S. Application Data

(60) Provisional application No. 62/187,602, filed on Jul. 1, 2015.

(51) Int. Cl.
*A61F 5/37*    (2006.01)
*A61M 16/08*    (2006.01)
(Continued)

(52) U.S. Cl.
CPC .............. *A61B 17/025* (2013.01); *A61F 5/37* (2013.01); *A61M 16/0493* (2014.02);
(Continued)

(58) Field of Classification Search
CPC .............................. A61B 90/16; A61B 17/025
See application file for complete search history.

(56) References Cited

U.S. PATENT DOCUMENTS

| | | | | |
|---|---|---|---|---|
| 900,541 A | * | 10/1908 | Holmes | A61C 9/0006 433/43 |
| 2,127,215 A | * | 8/1938 | Gwathmey | A61M 16/0488 128/207.14 |

(Continued)

FOREIGN PATENT DOCUMENTS

| | | |
|---|---|---|
| CN | 205251810 | 4/2016 |
| DE | 10216242 | 4/2003 |

(Continued)

OTHER PUBLICATIONS

Snore RX Review, [Mouthpiece for Snoring Reviews], unknown publication date; http://mouthpieceforsnoringreviews.com/snorerx-review/ accessed Apr. 25, 2015.

*Primary Examiner* — Christian A Sevilla
(74) *Attorney, Agent, or Firm* — Reising Ethington P.C.

(57) ABSTRACT

Airway assist device (AAD) is provided. The device includes an upper AAD component and a lower AAD component. The upper AAD component includes and upper tooth guide connected to an upper plate. The upper AAD component further includes an upper force receiving plate. The AAD also includes a lower AAD component. The lower AAD component includes a lower tooth guide connected to a lower plate. The lower AAD component further includes a lower force receiving plate. The upper and lower AAD components are connected in a way that allows relative movement between the two components between a neutral position and a plurality of extended positions to protrude and distract a patient's mandible. A ratchet mechanism inhibits movement of the lower plate from any extended position. The ratchet mechanism may be manually disengaged to allow the lower AAD component to return to the neutral position. The lower AAD component includes a chin guide.

(Continued)

The chin guide includes a chin support member that is engageable with a patient's chin.

20 Claims, 19 Drawing Sheets

(51) Int. Cl.
    *A61B 17/02*     (2006.01)
    *A61M 16/04*     (2006.01)
    *A61B 90/16*     (2016.01)

(52) U.S. Cl.
    CPC ...... *A61M 16/085* (2014.02); *A61M 16/0816* (2013.01); *A61M 16/0875* (2013.01); *A61B 90/16* (2016.02); *A61M 2202/0208* (2013.01); *A61M 2230/42* (2013.01); *A61M 2230/432* (2013.01)

(56) References Cited

U.S. PATENT DOCUMENTS

| | | |
|---|---|---|
| 2,521,084 A | 9/1950 | Oberto |
| 2,669,988 A | 2/1954 | Carpenter |
| 2,823,455 A | 2/1958 | Sprague |
| 2,882,893 A | 4/1959 | Godfroy |
| 3,132,647 A | 5/1964 | Corniello |
| 3,321,832 A | 5/1967 | Weisberg |
| 3,353,271 A | 11/1967 | Blechman |
| 3,461,858 A | 8/1969 | Michelson |
| 4,112,936 A | 9/1978 | Blachly |
| 4,169,473 A | 10/1979 | Samelson |
| 4,213,451 A * | 7/1980 | Swenson .................. A61B 1/24 600/215 |
| 4,226,234 A | 10/1980 | Gunderson |
| 4,270,531 A | 6/1981 | Blachly |
| 4,304,227 A | 12/1981 | Samelson |
| 4,382,783 A | 5/1983 | Rosenberg |
| 4,425,911 A | 1/1984 | Luomanen |
| 4,439,147 A | 3/1984 | Keys |
| 4,495,945 A | 1/1985 | Liegner |
| 4,505,672 A | 3/1985 | Kurz |
| 4,715,368 A | 12/1987 | George |
| 4,806,100 A | 2/1989 | Schainholz |
| 4,821,715 A | 4/1989 | Downing |
| 4,862,903 A | 9/1989 | Avenue |
| 4,901,737 A | 2/1990 | Toone |
| 4,928,710 A | 5/1990 | Avenue |
| 4,955,367 A | 9/1990 | Homsy |
| 4,969,822 A | 11/1990 | Summer |
| 4,978,323 A | 12/1990 | Freedman |
| 5,003,994 A | 4/1991 | Cook |
| 5,031,611 A | 7/1991 | Moles |
| 5,050,586 A | 9/1991 | Bonnell |
| 5,062,422 A | 11/1991 | Kinkeido |
| 5,066,226 A | 11/1991 | Summer |
| 5,082,007 A | 1/1992 | Adell |
| 5,092,346 A | 3/1992 | Meade |
| 5,117,816 A | 6/1992 | Shapiro |
| 5,154,609 A | 10/1992 | George |
| 5,176,594 A | 1/1993 | Lee |
| 5,176,618 A | 1/1993 | Freedman |
| 5,203,324 A | 4/1993 | Kinkeido |
| 5,273,032 A | 12/1993 | Borody |
| 5,277,202 A | 1/1994 | Hays |
| 5,305,741 A | 4/1994 | Moles |
| 5,313,960 A | 5/1994 | Tomasi |
| D348,932 S | 7/1994 | Jackson |
| 5,365,945 A | 11/1994 | Halstrom |
| 5,409,017 A | 4/1995 | Lowe |
| 5,413,095 A | 5/1995 | Weaver |
| 5,427,117 A | 6/1995 | Thornton |
| 5,462,066 A | 10/1995 | Snyder |
| 5,466,153 A | 11/1995 | Poindexter |
| 5,467,783 A | 11/1995 | Meade |
| 5,494,048 A | 2/1996 | Carden |
| 5,499,633 A | 3/1996 | Fenton |
| 5,513,634 A | 5/1996 | Jackson |
| 5,513,986 A | 5/1996 | Feltham |
| 5,524,639 A | 6/1996 | Lanier |
| 5,537,994 A | 7/1996 | Thornton |
| 5,566,683 A | 10/1996 | Thornton |
| 5,570,704 A | 11/1996 | Agre |
| 5,590,643 A | 1/1997 | Flam |
| 5,632,283 A | 5/1997 | Carden |
| 5,638,811 A | 6/1997 | David |
| 5,642,737 A | 7/1997 | Parks |
| 5,660,174 A | 8/1997 | Jacobelli |
| 5,682,632 A | 11/1997 | Cotroneo |
| 5,682,903 A | 11/1997 | Meade |
| 5,683,244 A | 11/1997 | Truax |
| 5,720,302 A | 2/1998 | Belfer |
| 5,752,510 A | 5/1998 | Goldstein |
| 5,752,822 A | 5/1998 | Robson |
| 5,755,219 A | 5/1998 | Thornton |
| 5,779,470 A | 7/1998 | Kussick |
| 5,794,627 A | 8/1998 | Frantz |
| 5,806,516 A | 9/1998 | Beattie |
| 5,810,013 A | 9/1998 | Belfer |
| 5,816,799 A | 10/1998 | Parker |
| 5,823,193 A | 10/1998 | Gottehrer |
| 5,829,441 A | 11/1998 | Kidd |
| 5,846,212 A | 12/1998 | Beeuwkes, III |
| 5,868,138 A | 2/1999 | Halstrom |
| 5,876,199 A | 3/1999 | Bergersen |
| 5,884,625 A | 3/1999 | Hart |
| 5,884,628 A | 3/1999 | Hilsen |
| 5,893,365 A | 4/1999 | Anderson |
| 5,921,241 A | 7/1999 | Belfer |
| 5,941,246 A | 8/1999 | Roopchand |
| 5,941,247 A | 8/1999 | Keane |
| 5,947,724 A | 9/1999 | Frantz |
| 5,950,624 A | 9/1999 | Hart |
| 5,954,048 A | 9/1999 | Thornton |
| 5,957,133 A | 9/1999 | Hart |
| 5,967,784 A | 10/1999 | Powers |
| 5,979,456 A | 11/1999 | Magovern |
| 5,983,892 A | 11/1999 | Thornton |
| 5,988,170 A | 11/1999 | Thomas |
| 6,041,784 A | 3/2000 | Halstrom |
| 6,055,986 A | 5/2000 | Meade |
| 6,109,265 A | 8/2000 | Frantz |
| 6,129,084 A | 10/2000 | Bergersen |
| 6,161,542 A | 12/2000 | Halstrom |
| 6,168,601 B1 | 1/2001 | Martini |
| 6,170,485 B1 | 1/2001 | Orrico |
| 6,171,314 B1 | 1/2001 | Rotramel |
| 6,200,285 B1 | 3/2001 | Towliat |
| 6,209,542 B1 | 4/2001 | Thornton |
| 6,244,865 B1 | 6/2001 | Salemi |
| 6,257,238 B1 | 7/2001 | Meah |
| 6,305,376 B1 | 10/2001 | Thornton |
| 6,325,064 B1 | 12/2001 | Thornton |
| 6,371,112 B1 | 4/2002 | Bibi |
| 6,374,824 B1 | 4/2002 | Thornton |
| 6,394,093 B1 | 5/2002 | Lethi |
| 6,405,729 B1 | 6/2002 | Thornton |
| 6,418,933 B1 | 7/2002 | Strong |
| 6,450,167 B1 | 9/2002 | David |
| 6,464,924 B1 | 10/2002 | Thornton |
| 6,505,625 B1 | 1/2003 | Uenishi |
| 6,505,626 B2 | 1/2003 | Belvedere |
| 6,505,627 B2 | 1/2003 | Belvedere |
| 6,505,628 B2 | 1/2003 | Belvedere |
| 6,508,251 B2 | 1/2003 | Belvedere |
| 6,510,853 B1 | 1/2003 | Belvedere |
| 6,516,805 B1 | 2/2003 | Thornton |
| 6,526,982 B1 | 3/2003 | Strong |
| 6,533,761 B2 | 3/2003 | Shepherd |
| 6,558,392 B1 | 5/2003 | Martini |
| 6,571,798 B1 | 6/2003 | Thornton |
| 6,584,975 B1 | 7/2003 | Taylor |
| 6,588,430 B2 | 7/2003 | Belvedere |
| 6,604,527 B1 | 8/2003 | Palmisano |

(56) References Cited

U.S. PATENT DOCUMENTS

| | | |
|---|---|---|
| 6,615,834 B2 | 9/2003 | Cresswell |
| 6,619,290 B1 | 9/2003 | Zacco |
| 6,626,169 B2 | 9/2003 | Gaitini |
| 6,637,436 B2 | 10/2003 | Farrel |
| 6,662,803 B2 | 12/2003 | Cresswell |
| 6,675,802 B1 | 1/2004 | Thornton |
| 6,675,806 B2 | 1/2004 | Belvedere |
| 6,675,808 B2 | 1/2004 | Karasic |
| 6,691,710 B2 | 2/2004 | Belvedere |
| 6,701,926 B2 | 3/2004 | Cresswell |
| 6,729,335 B1 | 5/2004 | Halstrom |
| 6,769,910 B1 | 8/2004 | Pantino |
| 6,789,541 B2 | 9/2004 | Cresswell |
| 6,789,543 B2 | 9/2004 | Cannon |
| 6,805,127 B1 | 10/2004 | Karasic |
| 6,679,257 B1 | 11/2004 | Gradon |
| 6,820,617 B2 | 11/2004 | Gradon |
| 6,832,610 B2 | 12/2004 | Cresswell |
| 6,845,774 B2 | 1/2005 | Gaskell |
| 6,860,270 B2 | 3/2005 | Sniadach |
| 6,877,513 B2 | 4/2005 | Barnett |
| 6,890,322 B2 | 5/2005 | Shepherd |
| 6,895,970 B1 | 5/2005 | Berghash |
| 6,926,007 B2 | 8/2005 | Frank |
| 6,932,598 B1 | 8/2005 | Anderson |
| 6,935,857 B1 | 8/2005 | Farrel |
| 6,951,218 B2 | 10/2005 | Cresswell |
| 6,969,366 B1 | 11/2005 | Reddick |
| 6,981,502 B2 | 1/2006 | Anthony |
| 6,988,888 B2 | 1/2006 | Cleary |
| 6,997,186 B2 | 2/2006 | Gradon |
| 7,001,180 B2 | 2/2006 | Bass |
| 7,004,172 B1 | 2/2006 | Zacco |
| 7,017,576 B2 | 3/2006 | Cresswell |
| 7,021,312 B2 | 4/2006 | Toussaint |
| 7,032,597 B1 | 4/2006 | Frank |
| 7,047,976 B2 | 5/2006 | Frank |
| 7,047,977 B2 | 5/2006 | Frank |
| 7,055,524 B1 | 6/2006 | Taimoorazy |
| 7,077,138 B2 | 7/2006 | Bateman |
| 7,077,646 B2 | 7/2006 | Hilliard |
| 7,080,648 B2 | 7/2006 | Frank |
| 7,124,756 B1 | 10/2006 | Frank |
| 7,124,757 B2 | 10/2006 | Frank |
| 7,128,071 B2 | 10/2006 | Brain |
| 7,134,436 B2 | 12/2006 | Frank |
| 7,143,767 B2 | 12/2006 | Zacco |
| 7,146,982 B2 | 12/2006 | Baratier |
| 7,174,895 B2 | 2/2007 | Thornton |
| 7,178,529 B2 | 2/2007 | Kownacki |
| 7,243,649 B2 | 7/2007 | Irlbeck |
| 7,263,998 B2 | 9/2007 | Miller |
| 7,278,420 B2 | 10/2007 | Armstead |
| 7,299,804 B2 | 11/2007 | Belvedere |
| 7,311,103 B2 | 12/2007 | Jeppesen |
| 7,328,698 B2 | 2/2008 | Barnett |
| 7,328,705 B2 | 2/2008 | Abramson |
| 7,331,349 B2 | 2/2008 | Neville |
| 7,336,065 B1 | 2/2008 | Zacco |
| 7,364,429 B2 | 4/2008 | Olivier |
| 7,399,182 B2 | 4/2008 | Olivier |
| 7,404,402 B2 | 7/2008 | Farrel |
| 7,448,388 B2 | 11/2008 | Diacopoulos |
| 7,500,480 B2 | 3/2009 | Andrews |
| 7,520,281 B1 | 4/2009 | Nahabedian |
| 7,581,542 B2 | 9/2009 | Abramson |
| 7,597,103 B2 | 10/2009 | Thornton |
| 7,607,439 B2 | 10/2009 | Hedge |
| 7,624,736 B2 | 12/2009 | Borody |
| 7,637,262 B2 | 12/2009 | Bailey |
| 7,650,885 B2 | 1/2010 | Paoluccio |
| D615,187 S | 5/2010 | Bowden |
| 7,712,468 B2 | 5/2010 | Hargadon |
| 7,721,741 B2 | 5/2010 | Thornton |
| 7,730,890 B2 | 6/2010 | Enoch |
| 7,730,891 B2 | 6/2010 | Lamberg |
| 7,748,386 B2 | 7/2010 | Thornton |
| 7,757,693 B2 | 7/2010 | Toussaint |
| 7,762,263 B2 | 7/2010 | Rose |
| 7,766,016 B2 | 8/2010 | Rosenblum |
| 7,793,661 B2 | 9/2010 | Macken |
| 7,810,502 B1 | 10/2010 | Nguyen |
| 7,810,503 B2 | 10/2010 | Magnin |
| 7,819,122 B2 | 10/2010 | Abramson |
| 7,823,590 B2 | 11/2010 | Bibi |
| 7,832,402 B2 | 11/2010 | Nelissen |
| 7,832,403 B2 | 11/2010 | Diacopoulos |
| 7,836,888 B2 | 11/2010 | Bhat |
| 7,836,889 B2 | 11/2010 | Kusukawa |
| 7,841,346 B2 | 11/2010 | Yan |
| 7,866,313 B2 | 1/2011 | Hoy |
| 7,866,314 B2 | 1/2011 | Hoy |
| 7,870,860 B2 | 1/2011 | Anthony |
| D631,969 S | 2/2011 | King |
| 7,882,842 B2 | 2/2011 | Bhat |
| D634,015 S | 3/2011 | King |
| 7,896,003 B2 | 3/2011 | Andrews |
| 7,896,007 B2 | 3/2011 | Brain |
| 7,905,232 B2 | 3/2011 | Cresswell |
| 7,935,065 B2 | 5/2011 | Bihari |
| 7,946,288 B2 | 5/2011 | Flynn |
| 7,951,102 B2 | 5/2011 | Gefen |
| 7,954,494 B1 | 6/2011 | Connor |
| 7,963,286 B2 | 6/2011 | Burdumy |
| 7,975,689 B2 | 7/2011 | Hauge |
| 7,980,248 B2 | 7/2011 | Bhat |
| 8,001,973 B2 | 8/2011 | Branscum, Jr. |
| 8,025,063 B2 | 9/2011 | Branscum, Jr. |
| 8,001,970 B2 | 10/2011 | Young |
| 8,028,704 B2 | 10/2011 | Reynolds, II |
| 8,028,705 B2 | 10/2011 | Hedge |
| 8,037,886 B2 | 10/2011 | Branscum, Jr. |
| 8,042,547 B2 | 10/2011 | Goldstein |
| 8,074,656 B2 | 12/2011 | Crowe |
| 8,082,923 B2 | 12/2011 | Doctors |
| 8,091,554 B2 | 1/2012 | Jiang |
| 8,100,126 B2 | 1/2012 | Cresswell |
| 8,104,467 B2 | 1/2012 | Napier |
| 8,109,271 B2 | 2/2012 | Vandine |
| 8,122,889 B2 | 2/2012 | Crowe |
| 8,122,890 B2 | 2/2012 | Crowe |
| 8,123,521 B1 | 2/2012 | Kopp |
| 8,127,769 B2 | 3/2012 | Kimani Mwangi |
| 8,136,529 B2 | 3/2012 | Kelly |
| 8,156,940 B2 | 4/2012 | Lee |
| 8,166,976 B2 | 5/2012 | Lieberman |
| 8,191,553 B2 | 6/2012 | Stone |
| 8,205,617 B2 | 6/2012 | Stygar |
| 8,215,312 B2 | 7/2012 | Garabadian |
| 8,220,461 B1 | 7/2012 | Guerra |
| 8,226,407 B2 | 7/2012 | Hanewinkel, III |
| 8,251,069 B2 | 8/2012 | Burdumy |
| 8,256,426 B2 | 9/2012 | Abramson |
| 8,262,596 B2 | 9/2012 | Gefen |
| 8,297,275 B2 | 10/2012 | Ogilvie |
| 8,316,857 B2 | 11/2012 | Thornton |
| 8,316,858 B2 | 11/2012 | Thornton |
| 8,321,884 B2 | 11/2012 | Fuselier |
| 8,336,550 B2 | 12/2012 | Goldstein |
| 8,336,553 B2 | 12/2012 | Bhat |
| 8,347,890 B2 | 1/2013 | Hedge |
| 8,356,592 B2 | 1/2013 | Andrews |
| 8,356,603 B2 | 1/2013 | Thornton |
| 8,372,020 B2 | 2/2013 | Bihari |
| 8,413,658 B2 | 4/2013 | Williams |
| 8,443,797 B2 | 5/2013 | Hauge |
| 8,474,458 B1 | 7/2013 | Yadven |
| 8,485,194 B2 | 7/2013 | Guerra |
| 8,505,540 B2 | 8/2013 | Crowe |
| 8,517,029 B2 | 8/2013 | Nelissen |
| 8,534,278 B2 | 9/2013 | Colman |
| 8,544,472 B2 | 10/2013 | Gaskell |
| 8,550,816 B2 | 10/2013 | Hanewinkel, III |
| 8,555,886 B2 | 10/2013 | Colman |

(56) References Cited

U.S. PATENT DOCUMENTS

| | | |
|---|---|---|
| 8,573,223 B2 | 11/2013 | Crowe |
| 8,573,224 B2 | 11/2013 | Thornton |
| 8,578,937 B2 | 11/2013 | Bhat |
| 8,602,029 B2 | 12/2013 | Cresswell |
| 8,607,796 B2 | 12/2013 | Thornton |
| 8,613,279 B2 | 12/2013 | Cresswell |
| 8,613,283 B2 | 12/2013 | Hedge |
| 8,631,800 B2 | 1/2014 | Clark |
| 8,640,692 B2 | 2/2014 | Matioc |
| 8,646,455 B2 | 2/2014 | Lieberman |
| 8,656,925 B2 | 2/2014 | Davis |
| 8,656,926 B2 | 2/2014 | Doctors |
| 8,656,922 B2 | 3/2014 | Crowe |
| 8,662,084 B2 | 3/2014 | Auley |
| 8,671,946 B2 | 3/2014 | Auley |
| 8,667,970 B2 | 4/2014 | Crowe |
| 8,684,006 B2 | 4/2014 | Morgan |
| 8,684,007 B2 | 4/2014 | Timmons |
| 8,684,919 B2 | 4/2014 | Anca |
| 8,701,672 B2 | 4/2014 | Crowe |
| 8,714,157 B2 | 5/2014 | Cresswell |
| 8,739,794 B2 | 6/2014 | Cutler |
| 8,757,164 B2 | 6/2014 | Abramson |
| 8,770,189 B2 | 7/2014 | Colman |
| 8,783,259 B2 | 7/2014 | Spencer |
| 8,783,260 B2 | 7/2014 | Remmers et al. |
| 8,783,261 B2 | 7/2014 | Auley |
| 8,783,263 B2 | 7/2014 | Baldwin |
| 8,813,753 B2 | 8/2014 | Bhat |
| 8,820,320 B2 | 9/2014 | Filipi |
| 8,833,374 B2 | 9/2014 | Fallon |
| 8,839,793 B2 | 9/2014 | Diaz |
| 8,857,439 B2 | 10/2014 | Hedge |
| 8,875,713 B2 | 11/2014 | Metz |
| 8,881,733 B1 | 11/2014 | Harkins |
| 8,893,719 B2 | 11/2014 | Madjar |
| 8,910,626 B2 | 12/2014 | Andrews |
| 8,931,477 B2 | 1/2015 | Ogilvie |
| 8,931,486 B2 | 1/2015 | Halstrom |
| 8,931,488 B2 | 1/2015 | Evans |
| 8,950,027 B2 | 2/2015 | Kitahara |
| 8,973,573 B2 | 3/2015 | Filipi |
| 9,050,198 B2 | 6/2015 | Kallen |
| 9,060,680 B2 | 6/2015 | Colman |
| 9,072,612 B2 | 7/2015 | Sethi |
| 9,095,454 B2 | 8/2015 | Fleury |
| 9,119,928 B2 | 9/2015 | Hauge |
| 9,132,254 B2 | 9/2015 | Anca |
| 9,138,169 B2 | 9/2015 | Beard |
| 9,144,512 B2 | 9/2015 | Wagner |
| 9,144,655 B2 | 9/2015 | Cresswell |
| 9,155,855 B2 | 10/2015 | Haycock |
| 9,173,765 B2 | 11/2015 | Stone |
| 9,186,473 B2 | 11/2015 | Colman |
| 9,192,454 B2 | 11/2015 | Klein |
| 9,204,991 B1 | 12/2015 | Harkins |
| 9,220,629 B2 | 12/2015 | Koike |
| 9,220,653 B2 | 12/2015 | Israel |
| 9,237,940 B2 | 1/2016 | Koeklue |
| 9,241,825 B2 | 1/2016 | Crowe |
| 9,265,681 B1 | 2/2016 | Bell |
| D752,760 S | 3/2016 | Raad |
| 9,333,413 B2 | 5/2016 | Evans |
| 9,339,410 B2 | 5/2016 | Smith |
| 9,339,621 B2 | 5/2016 | Cresswell |
| D760,889 S | 7/2016 | Evans |
| 9,408,743 B1 | 8/2016 | Wagner |
| 9,414,896 B2 | 8/2016 | Giffey |
| 9,439,802 B2 | 9/2016 | Wagner |
| 9,445,938 B1 | 9/2016 | Wagner |
| 9,545,330 B2 | 1/2017 | Fleury |
| 9,545,331 B2 | 1/2017 | Ingemarsson Matzen |
| 9,545,332 B2 | 1/2017 | Luco |
| 9,575,739 B2 | 2/2017 | Bell |
| 9,585,785 B2 | 3/2017 | Hofmann |
| 9,610,189 B2 | 4/2017 | Heinonen |
| 9,610,190 B2 | 4/2017 | Crowe |
| 9,615,964 B2 | 4/2017 | Rogers |
| 9,629,975 B1 | 4/2017 | Kane |
| 9,655,692 B2 | 5/2017 | Lucas |
| 9,655,766 B2 | 5/2017 | Wood |
| 9,655,768 B2 | 5/2017 | Crowe |
| 9,669,174 B2 | 6/2017 | Hoy |
| 9,687,623 B2 | 6/2017 | Colman |
| 9,655,695 B2 | 7/2017 | Ross |
| 9,707,121 B2 | 7/2017 | Wood |
| 9,707,368 B2 | 7/2017 | Cresswell |
| 9,717,975 B2 | 8/2017 | Evans |
| 9,744,006 B2 | 8/2017 | Ross |
| 9,744,070 B2 | 8/2017 | Chung |
| 9,802,021 B2 | 10/2017 | Haycock |
| 9,820,881 B2 | 11/2017 | Aarestad |
| 9,820,882 B2 | 11/2017 | Kuhns |
| D805,644 S | 12/2017 | Lesser |
| 9,844,424 B2 | 12/2017 | Ali |
| 9,849,259 B2 | 12/2017 | Colman |
| 9,867,753 B2 | 1/2018 | Arauz |
| 9,867,957 B2 | 1/2018 | Colman |
| 2002/0069872 A1 | 6/2002 | Smith |
| 2003/0015198 A1 | 1/2003 | Britt |
| 2005/0028826 A1 | 2/2005 | Palmisano |
| 2005/0051178 A1 | 3/2005 | Sawford |
| 2005/0175954 A1 | 8/2005 | Zacher |
| 2005/0274386 A1 | 12/2005 | Macken |
| 2005/0274387 A1 | 12/2005 | Macken |
| 2006/0174897 A1 | 8/2006 | Sarkisian |
| 2006/0201520 A1 | 9/2006 | Christensen, III |
| 2006/0207597 A1 | 9/2006 | Wright |
| 2007/0006878 A1 | 1/2007 | Mackey |
| 2007/0068534 A1 | 3/2007 | Bailey |
| 2007/0079833 A1 | 4/2007 | Lamberg |
| 2007/0089752 A1 | 4/2007 | Christensen |
| 2007/0113844 A1 | 5/2007 | Garren |
| 2007/0135770 A1 | 6/2007 | Cropper |
| 2007/0287598 A1 | 12/2007 | Christensen, III |
| 2008/0053434 A1 | 3/2008 | Atkinson |
| 2008/0072915 A1 | 3/2008 | Nelissen |
| 2008/0115791 A1 | 5/2008 | Heine |
| 2008/0149110 A1 | 6/2008 | Baldwin |
| 2008/0149114 A1 | 6/2008 | Baldwin |
| 2008/0153056 A1 | 6/2008 | Baldwin |
| 2008/0153057 A1 | 6/2008 | Baldwin |
| 2008/0156324 A1 | 7/2008 | Hoy |
| 2008/0173313 A1 | 7/2008 | Neville |
| 2008/0190437 A1 | 8/2008 | Hervy Auboiron |
| 2008/0257358 A1 | 10/2008 | Alessandrini |
| 2009/0032030 A1 | 2/2009 | Callender |
| 2009/0036889 A1 | 2/2009 | Callender |
| 2009/0095309 A1 | 4/2009 | Derrick et al. |
| 2009/0098508 A1 | 4/2009 | Baldwin |
| 2009/0145442 A1 | 6/2009 | Hecox |
| 2009/0163838 A1 | 6/2009 | Hecox |
| 2009/0177124 A1 | 7/2009 | Oronsky |
| 2010/0030027 A1 | 2/2010 | Bastid |
| 2010/0065066 A1 | 3/2010 | Hamburg |
| 2010/0224198 A1 | 9/2010 | Ayuse |
| 2010/0261133 A1 | 10/2010 | Lax |
| 2010/0262033 A1 | 10/2010 | Colman |
| 2010/0307511 A1 | 12/2010 | Meade |
| 2011/0168188 A1 | 7/2011 | Moore |
| 2011/0195376 A1 | 8/2011 | Boyd |
| 2011/0253150 A1 | 10/2011 | Young |
| 2012/0041440 A1 | 2/2012 | Waddell |
| 2012/0204865 A1 | 8/2012 | Filipi |
| 2013/0098373 A1 | 4/2013 | Carlone |
| 2013/0112210 A1 | 5/2013 | Stein |
| 2013/0118507 A1 | 5/2013 | Chappuis |
| 2013/0263865 A1 | 10/2013 | Khast |
| 2014/0007868 A1 | 1/2014 | Eaton |
| 2014/0048078 A1 | 2/2014 | Aahnblad |
| 2014/0076332 A1 | 3/2014 | Luco |
| 2014/0130809 A1 | 5/2014 | Clark |
| 2014/0144450 A1 | 5/2014 | Aarestad |
| 2014/0216469 A1 | 8/2014 | Keropian |

(56) References Cited

U.S. PATENT DOCUMENTS

| | | |
|---|---|---|
| 2014/0275784 A1 | 9/2014 | Joyce |
| 2014/0349243 A1 | 11/2014 | Metz |
| 2014/0352700 A1 | 12/2014 | Ingemarsson-Matzen |
| 2015/0007830 A1 | 1/2015 | Bruehlmann |
| 2015/0020812 A1 | 1/2015 | Keropian |
| 2015/0164682 A1 | 6/2015 | Grosse |
| 2015/0164726 A1 | 6/2015 | Plott |
| 2015/0182374 A1 | 7/2015 | Stenberg |
| 2015/0190599 A1 | 7/2015 | Colman |
| 2015/0238280 A1 | 8/2015 | Ali |
| 2015/0245940 A1 | 9/2015 | Hardcastle |
| 2016/0022429 A1 | 1/2016 | Colman |
| 2016/0058275 A1 | 3/2016 | Hu |
| 2016/0101008 A1 | 4/2016 | Stone |
| 2016/0120619 A1 | 5/2016 | Bons |
| 2016/0184127 A1 | 6/2016 | Kitahara |
| 2016/0287429 A1 | 10/2016 | Lin |
| 2016/0287831 A1 | 10/2016 | Haycock |
| 2016/0361192 A1 | 12/2016 | Gerschman |
| 2016/0367394 A1 | 12/2016 | Wagner |
| 2017/0000586 A1 | 1/2017 | Lesser |
| 2017/0000643 A1 | 1/2017 | Gelb |
| 2017/0007795 A1 | 1/2017 | Cataldo |
| 2017/0049607 A1 | 2/2017 | McAuley |
| 2017/0087003 A1 | 3/2017 | Luco |
| 2017/0128256 A1 | 5/2017 | Metz |
| 2017/0202644 A1 | 7/2017 | Ross |
| 2017/0209238 A9 | 7/2017 | Ali |
| 2017/0231723 A1 | 8/2017 | Lucas |
| 2017/0266402 A1 | 9/2017 | Hoy |
| 2017/0143537 A1 | 11/2017 | Kuhns |

FOREIGN PATENT DOCUMENTS

| | | |
|---|---|---|
| EP | 3209241 | 8/2017 |
| FR | 2820307 | 8/2004 |
| JP | 4115012 | 7/2008 |
| KR | 101479025 | 1/2015 |
| WO | 07014429 | 2/2007 |
| WO | 15127443 | 8/2015 |
| WO | 17149523 | 9/2017 |
| WO | 17152030 | 9/2017 |

\* cited by examiner

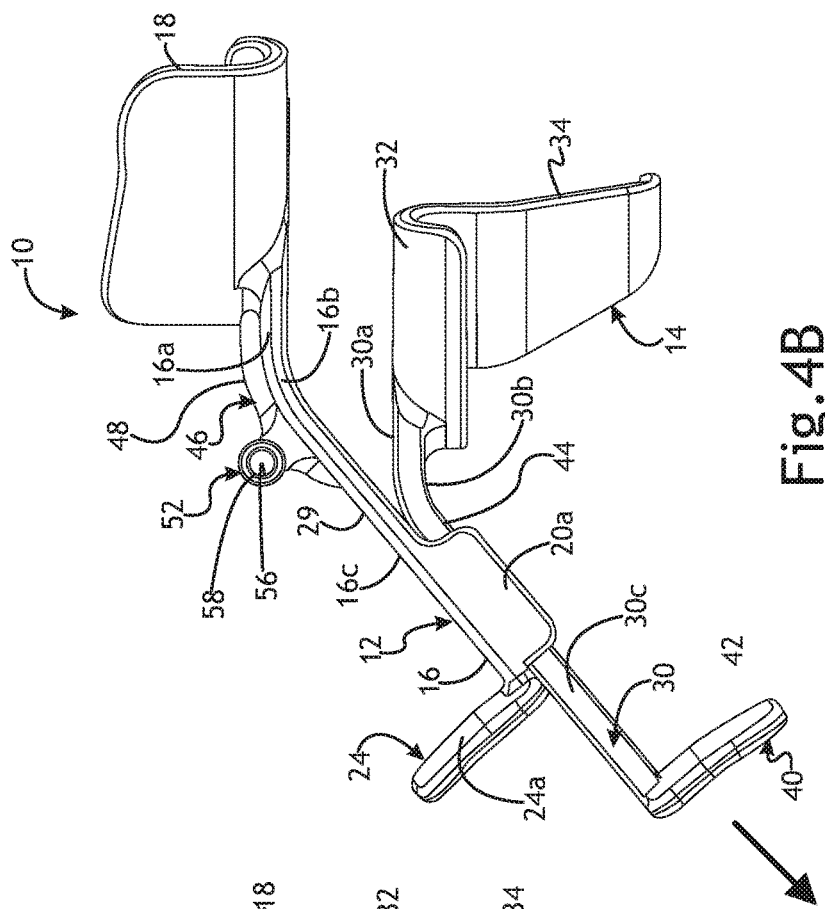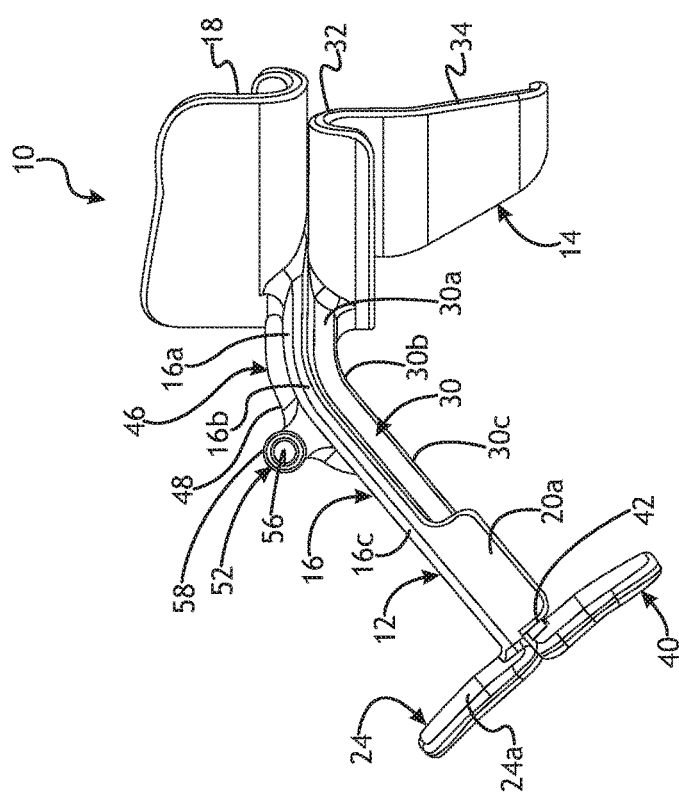

AIRWAY ASSIST DEVICE AND METHOD

This is a non-provisional patent application which claims the benefit of U.S. Provisional Patent Application Ser. No. 62/187,602 filed Jul. 1, 2015, the disclosure of which is incorporated herein by reference in its entirety.

FIELD OF THE INVENTION

The present invention relates generally to an airway assist device and method.

BACKGROUND OF THE INVENTION

Maintaining a patient airway is essential and a prime tenet of the ABC's of resuscitation. Numerous human conditions can create upper airway obstruction that mandate interventional treatment. Some conditions that can create upper airway obstructions include conditions related to anesthesia, obstructive sleep apnea (OSA), cardiopulmonary collapse and convulsions. Multiple strategies exist to maintain an airway. These include Esmarch technique (bimanual jaw-thrust), nasopharyngeal (Wendl) airways, oropharyngeal (Guedel) airways, bag and mask, supraglottic airway (SGA) that include the laryngeal mask airway (LMA), endotracheal intubation and mandibular advancement/repositioning devices/appliances (MAD's/MRA's).

It would be desirable to provide a device and method to maintain airway patency, and particularly the oropharynx and retropalatal space by providing an improved device that allows for lower jaw protrusion and distraction. It may also be desirable to have a device to maintain airway patency that can also supply oxygen and/or monitor end-tidal carbon dioxide wave form and respiratory rate.

SUMMARY OF THE INVENTION

According to an embodiment, there is provided an airway assist device (AAD). The AAD comprises a first airway assist device component including an upper plate and an upper tooth guide. The upper plate includes a first portion and a descending portion connected to the first portion. The first portion extends at an angle relative to the first portion. The AAD further comprises a second airway assist device component including a lower plate and a lower tooth guide connected to the lower plate. The lower plate includes a first portion and a descending portion connected to the first portion and extending at an angle relative to the first portion. The first airway assist device component is connected with the second airway assist device component to allow relative movement between the first and second airway assist device components between a neutral position and at least one extended position. A ratchet mechanism acts between the first and second airway assist device components. The ratchet assembly allows for movement of the second airway assist device component from the neutral position to an extended position and inhibits movement of the second airway assist device component from an extended position toward the neutral position.

According to an embodiment, there is provided an airway assist device (AAD). The AAD comprises a first airway assist device component including an upper plate and an upper tooth guide. The upper plate includes a first portion and a descending portion connected to the first portion. The first portion extends at an angle relative to the first portion. The AAD further comprises a second airway assist device component including a lower plate and a lower tooth guide connected to the lower plate. The lower plate includes a first portion and a descending portion connected to the first portion and extending at an angle relative to the first portion. The first airway assist device component is connected with the second airway assist device component to allow relative movement between the first and second airway assist device components between a neutral position and at least one extended position. A ratchet mechanism acts between the first and second airway assist device components. The ratchet assembly allows for movement of the second airway assist device component from the neutral position to an extended position and inhibits movement of the second airway assist device component from an extended position toward the neutral position. The AAD further comprises a chin guide comprising a slider member, a first wall and a chin support connected to the slider member. The slider member is moveable relative to the first wall between at least one extended position and at least one non-extended position. The AAD further comprises a second ratchet mechanism acting between the first wall and the slider member, the second ratchet mechanism to allow for movement of the slider member from an extended position to a non-extended position and inhibit movement of the slider member from a non-extended position to an extended position.

According to an embodiment, there is provided a method of maintaining airway patency. The method comprises positioning an upper tooth guide of a first airway assist device component relative to a patient and positioning a lower tooth guide of a second airway assist device component relative to a patient. A force is applied to the second airway assist device component in a direction downwardly and away from the patient to move the second airway assist device component relative to the first airway assist device component to protrude and distract the patient's mandible; and holding the second airway assist device component in an extended position by a ratchet mechanism.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4a is a side view the embodiment of FIG. 1 in a neutral position;

FIG. 4b is a side view the embodiment of FIG. 1 in an extended position;

DETAILED DESCRIPTION OF THE PREFERRED EMBODIMENTS

The following description of the preferred embodiment(s) is merely exemplary in nature and is in no way intended to limit the invention, its application, or its uses.

Figure 1:
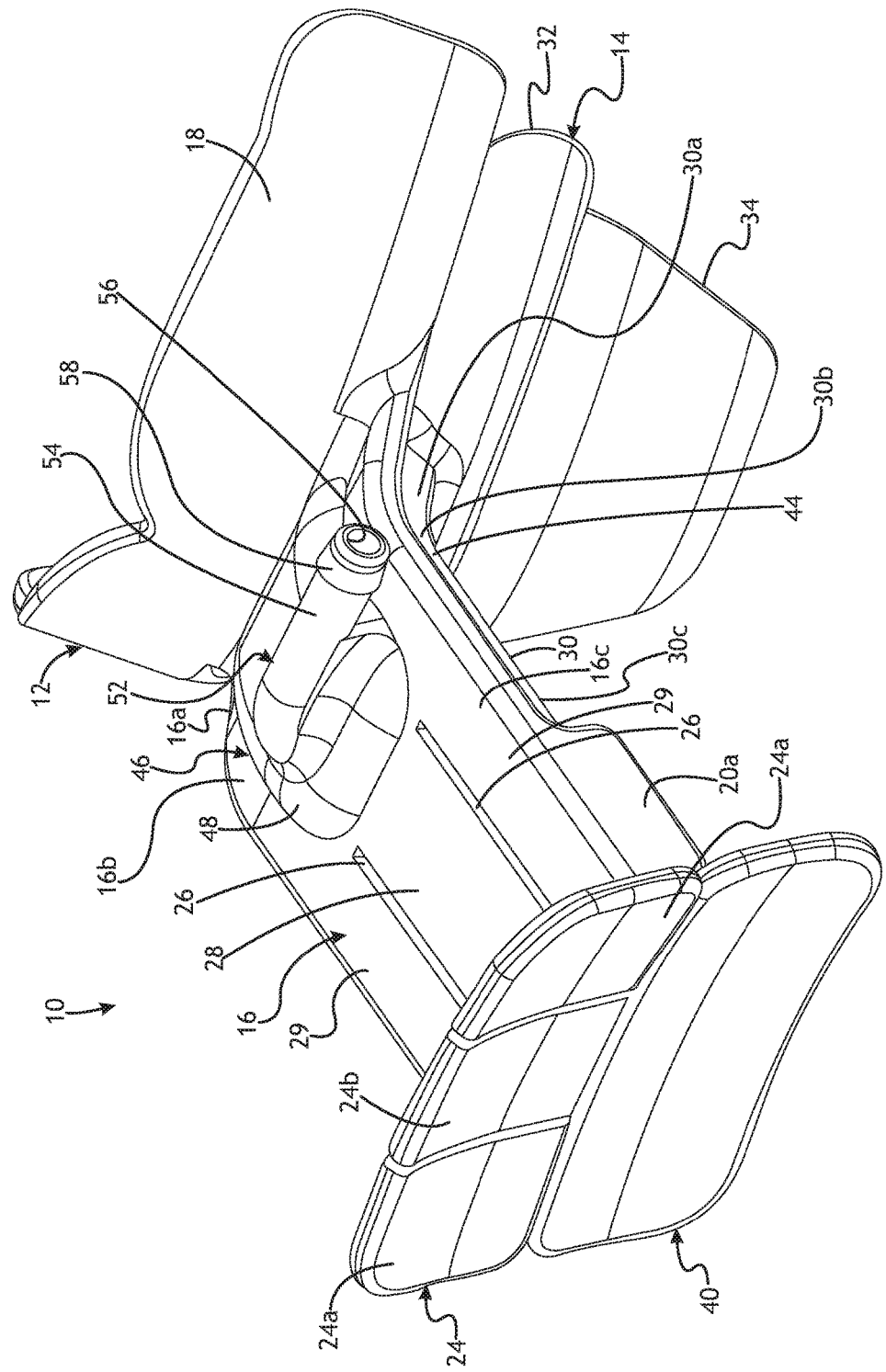
FIG. 1 is a perspective view of an embodiment in a neutral position.
Figure 2:
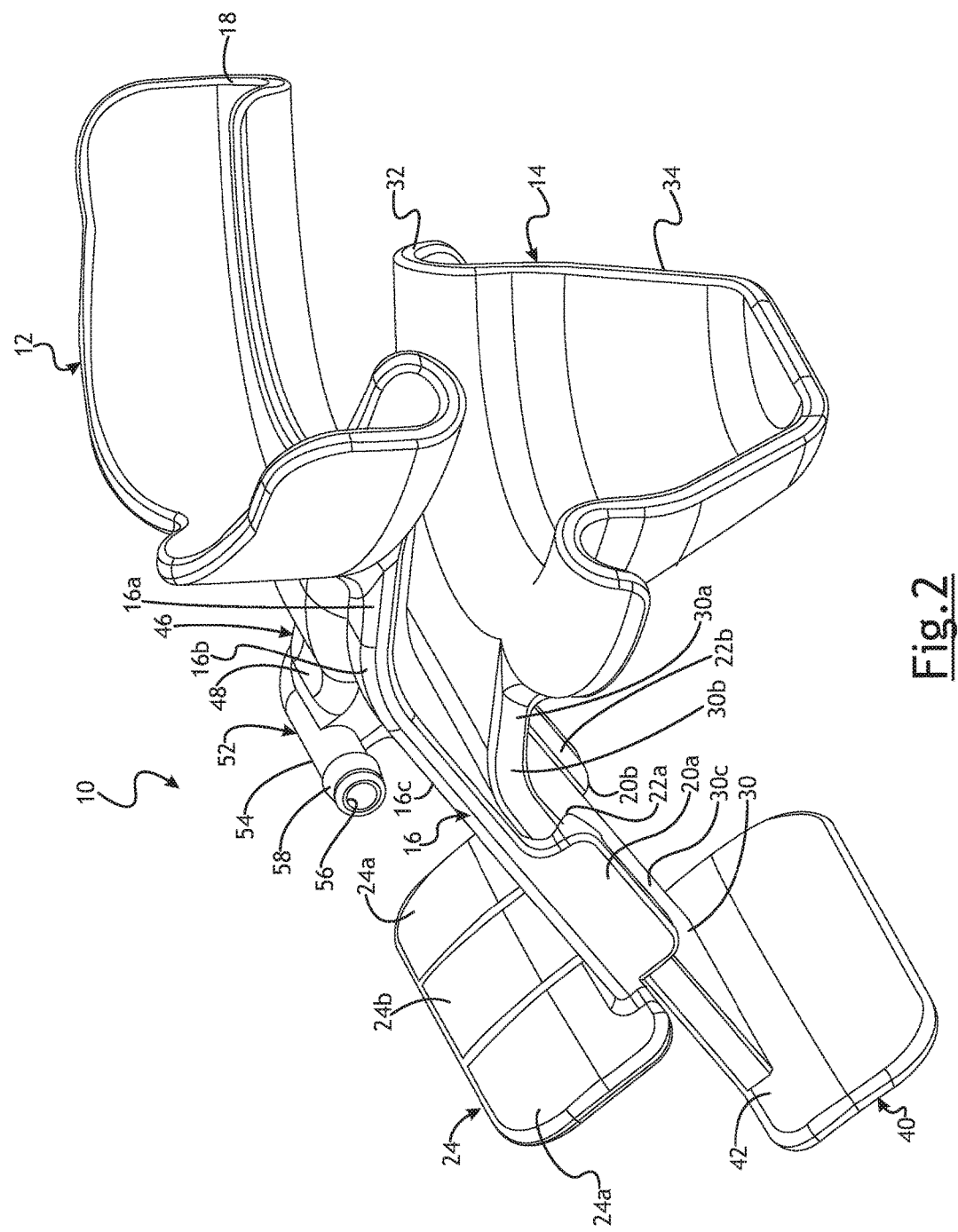
FIG. 2 is a perspective view the embodiment of FIG. 1 in an extended position.
Figure 3:
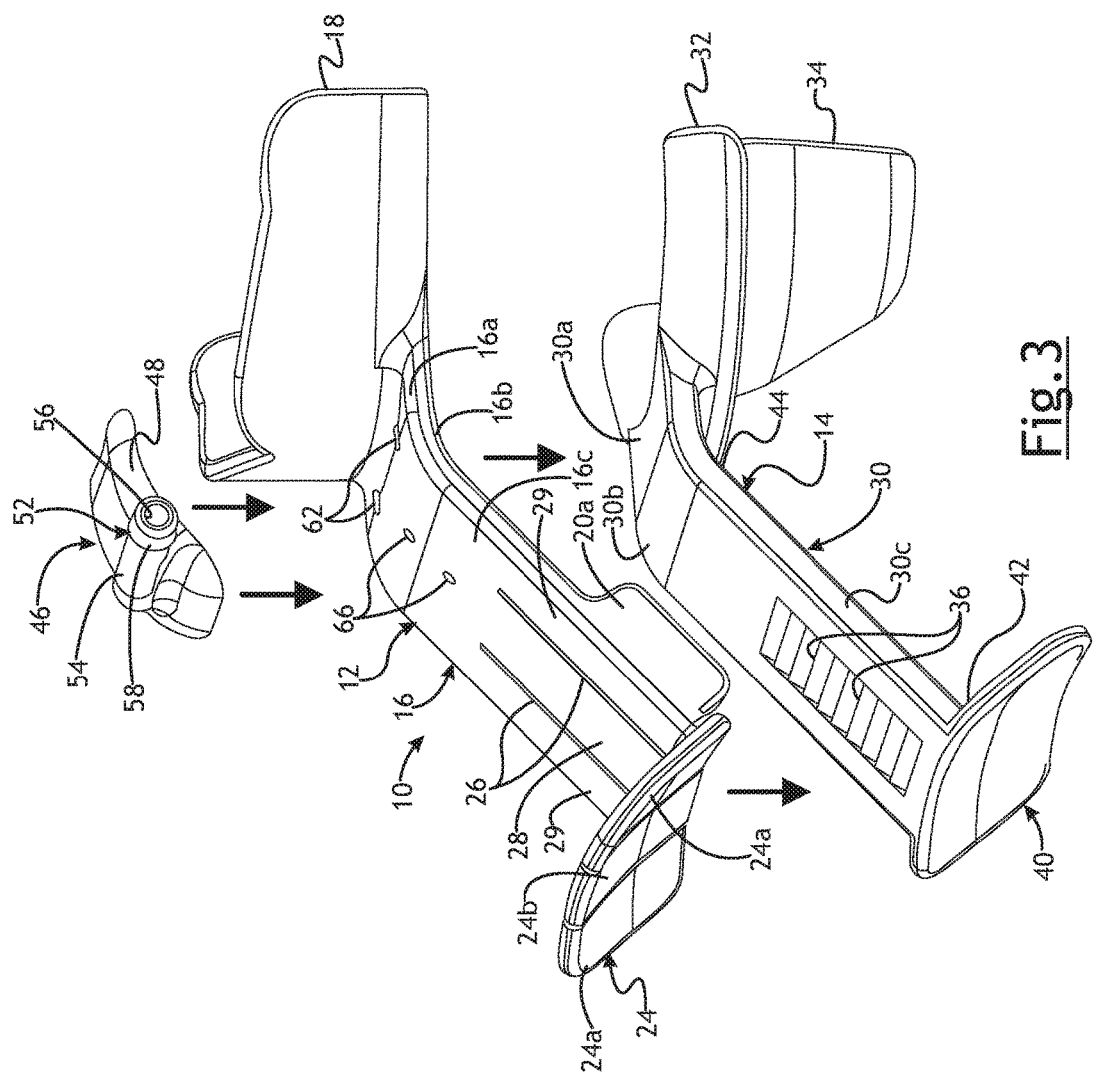
FIG. 3 is an exploded view the embodiment of FIG. 1.

An embodiment of an airway assist device (AAD) is generally shown at 10 in FIGS. 1-9. The AAD 10 may be useful to allow for lower jaw protrusion and distraction that opens the posterior airway (PAW) space and may also allow for supplemental oxygen delivery. As best shown in FIG. 3, the AAD 10 may comprise a first or upper AAD component generally indicated at 12 and a second or lower AAD component, generally indicated at 14. The upper AAD component 12 may comprise an injection molded component. The lower AAD component 14 may comprise an injection molded component. The upper AAD component 12 and lower AAD component 14 may comprise any suitable material.

In the embodiment shown, the upper AAD component 12 has an upper plate generally indicated at 16. The upper plate 16 is preferably connected to an upper tooth guide 18. The upper tooth guide 18 preferably envelopes a dentate or edentulous alveolar ridge of the patient. All or part of the upper tooth guide 18 may be covered with a relatively soft material. By way of non-limiting example, the upper tooth guide 18 may be overmolded with a relatively soft urethane material.

As shown, the upper plate 16 extends from the upper tooth guide 18. The upper plate 16 is preferably generally rectangular when viewed from the top. The upper plate 16 preferably extends downwardly and outwardly from the upper tooth guide 18. The upper plate 16 therefore may extend downwardly, in the direction of the patient's chin, and outwardly, away from the patient's face. While the upper plate 16 is described as being generally rectangular, it will be appreciated that the upper plate 16 may take any suitable geometrical configuration.

As shown in FIGS. 4a and 4b, the upper plate 16 may be curved when viewed from the side. That is, the upper plate may extend horizontally from the upper tooth guide 18 and may then curve downwardly at an angle relative to the horizontal portion. More specifically, the upper plate 16 may include a portion 16a that extends outwardly and generally perpendicularly with respect to the patient from the upper tooth guide 18. The upper plate 16 may also include a curved portion 16b. The upper plate 16 may also include a descending portion 16c that extends from the curved portion. The curved portion 16b may form an angle of between about 120 degrees and about 165 degrees between the portion 16a and the descending portion 16c. This represents an angle of the descending portion 16c being between about 35 degrees and 75 degrees with respect to the patient. In one preferred embodiment, the curved section 16b may form an angle of between about 135 degrees and 158 degrees between the portion 16a and the descending portion 16c. This represents an angle of the descending portion 16c of between about 45 degrees and 68 degrees with respect to the patient. In another preferred embodiment, the curved section 16b may form an angle of about 158 degrees between the portion 116a and the descending portion 16c. This represents an angle of the descending portion 16c of about 68 degrees with respect to the patient. It will be appreciated that any suitable angle may be used.

As best seen in FIG. 2, the upper plate 16 preferably includes a pair of legs 20a, 20b depending therefrom. Preferably, the legs 20a and 20b are similarly constructed. The legs 20a, 20b depend from opposite sides of the upper plate 16. Each leg 20a, 20b has a lip 22a, 22b extending therefrom respectively. Each lip 22a and 22b extends in a direction inwardly or toward the direction of the centerline of the upper plate 16. The upper surfaces of each lip 22a and 22b are preferably generally rectangular and are preferably relatively smooth and parallel with the bottom surface of the upper plate. The bottom surfaces of each lip 22a and 22b may be angled or ramped. The bottom side of the upper plate 16, legs 20a, 20b and lips 22a and 22b preferably cooperate to form a guide to receive a lower plate 30, as will be described in more detail below.

The upper plate 16 includes a pair of spaced apart slits 26. A center portion 28 of the upper plate 16 is thereby formed between the slits 26. Outer portions 29 of the upper plate are adjacent the slits 26. The legs 20a, 20b depend from the respective outer portions 29. The center portion 28 may flex relative to the outer portion 29 of the upper plate 16 in the vertical direction as the AAD 10 is best shown in FIG. 7.

Figure 5:
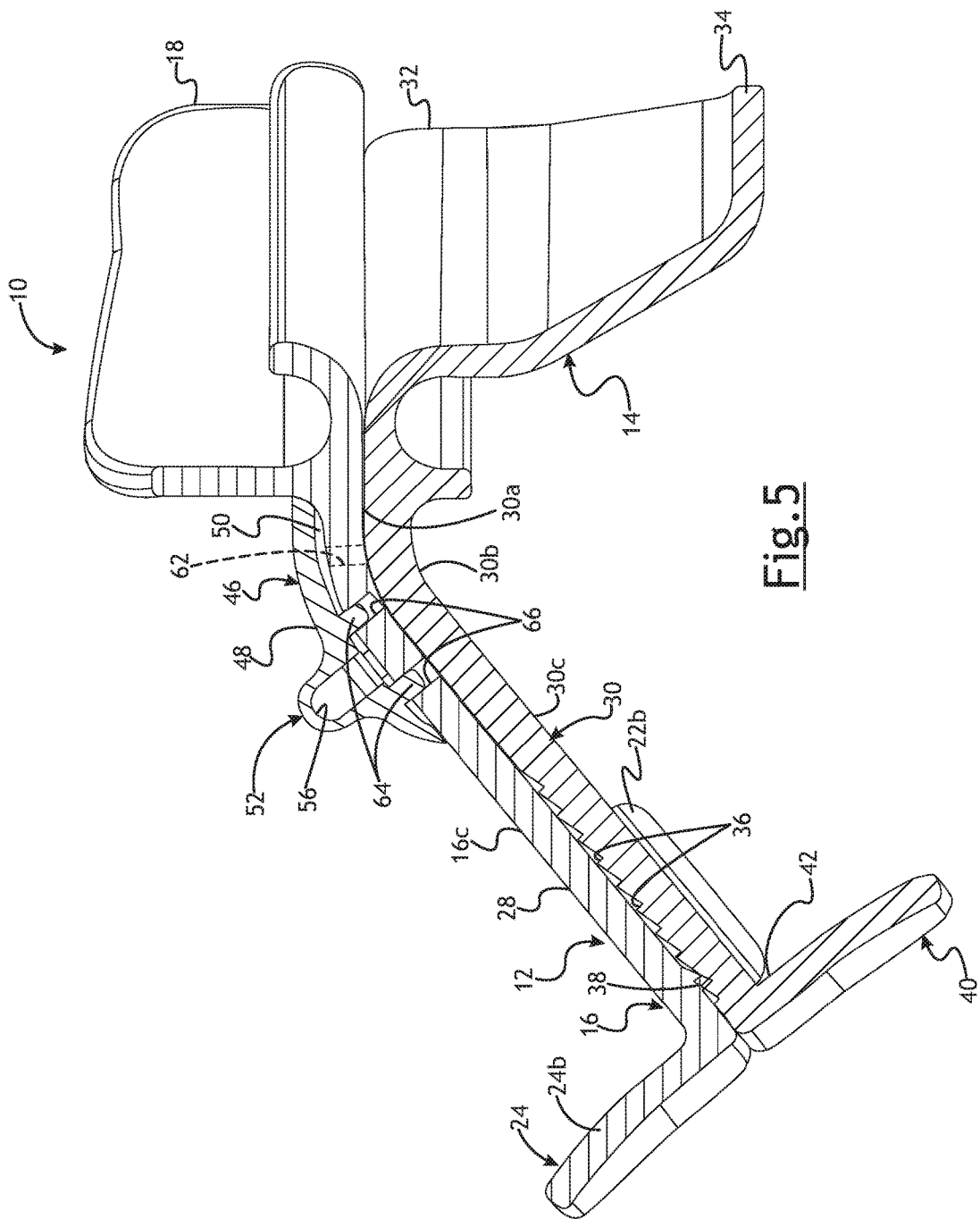
FIG. 5 is a cross-sectional view of the embodiment of FIG. 1.
Figure 6:
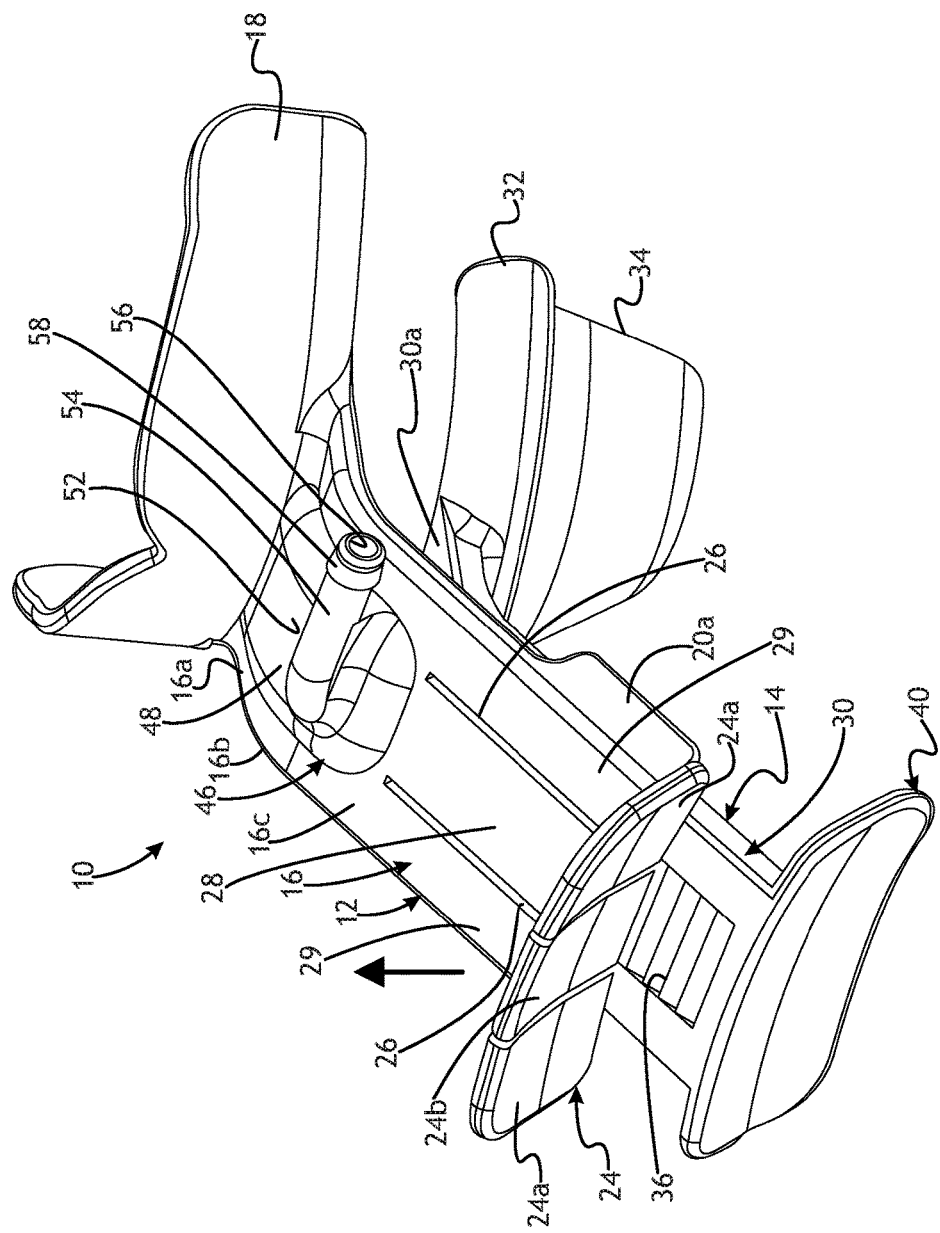
FIG. 6 is a perspective view of the embodiment of FIG. 1 in an extended position.
Figure 7:
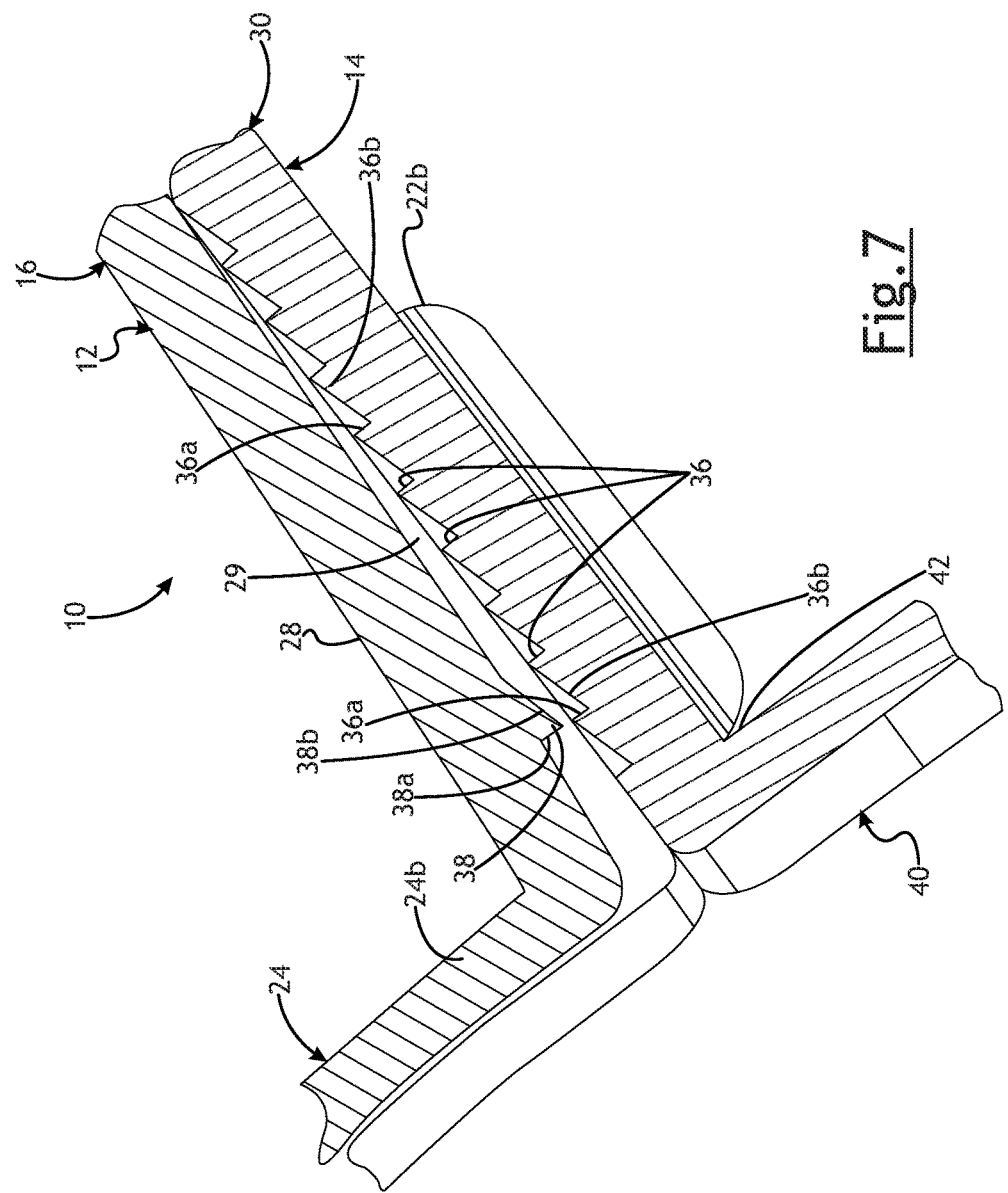
FIG. 7 is a cross-sectional view, partially broken away, showing the ratchet mechanism disengaged.

As best seen in FIGS. 5 and 7, the center portion 28 of the upper plate 16 further includes a pawl 38 extending from the bottom surface thereof. The pawl 38 is part of a ratchet mechanism that is used to maintain the AAD 10 in an appropriate extended position, as will be described in more detail below.

The upper AAD component 12 further includes an upper force receiving plate generally indicated at 24. In the embodiment shown, the upper force receiving plate 24 extends transversely and preferably perpendicularly to the upper plate 16 and is connected thereto. As shown, the upper force receiving plate 24 extends upwardly from the upper plate 16. The upper force receiving plate 24 may be generally curved as shown in the Figures. It will be appreciated, however, that the upper force receiving plate 24 may take any suitable geometric configuration. In certain embodiments, the upper force receiving plate 24 may even constitute the end of the upper plate 16. It will further be appreciated that the upper force receiving plate 24 may be disposed at locations on the upper plate 16 other than at the end thereof.

The upper force receiving plate 24 is preferably divided into a plurality of sections; two outermost sections 24a and a center section 24b. As shown in FIG. 2, the slits 26 are preferably contiguous from the upper plate 16 and onto the upper force receiving plate 24. Each of the sections 24a is preferably secured to the outer portions 29 of the upper plate 16. The center section 24b is preferably secured to the center portion 28 of the upper plate 16. In one embodiment as shown, the outermost sections 24a and center section 24b are integrally formed with the outer portions 29 and center portion 28, respectively of the upper plate 16. The center section 24b can flex in the direction away from the lower plate 30, as is best shown in FIG. 7, relative to the outermost sections 24a and along with the center portion 28 of the upper plate 16.

The upper AAD component 12 is preferably molded as a single piece. And as set forth above a relatively softer material such as urethane may be molded over, or otherwise placed over, the upper tooth guide 18. The upper AAD component 12 is preferably rigid. It will be appreciated, however that the legs 20a, 20b may flex slightly relative to the upper plate 16 when AAD is being assembled, and the center portion 28 and center section 24b can flex relative to the outer portions 29 of the upper plate 16 and the outermost sections 24a of the upper force receiving plate 24, respectively.

In the embodiment shown in FIGS. 1-9, the lower AAD component 14 has a lower plate generally indicated at 30. The lower plate 30 is preferably connected to a lower tooth guide 32. The lower tooth guide 32 further may include a lower dental guard 34 that extends such that it may engage the lingual aspect of the mandible of a patient. All or part of the lower tooth guide 32 and dental guard 34 may be covered with a relatively soft material. By way of non-limiting example, the lower tooth guide 32 and/or the lower dental guard 34 may be overmolded with a relatively soft urethane material.

As best seen in FIG. 3, the lower plate 30 extends from the lower tooth guide 32. The lower plate 30 preferably extends downwardly and outwardly from the lower tooth guide 32. The lower plate 30 therefore may extend downwardly, in the direction of the patient's chin, and outwardly, away from the patient's face. The lower plate 30 is preferably generally rectangular. While the lower plate 30 is described as being generally rectangular, it will be appreciated that the lower plate 30 may take any suitable geometrical configuration. As shown in FIGS. 4a and 4b, the lower plate 30 may be curved when viewed from the side. That is, the lower plate 30 may extend horizontally from the lower tooth guide 32 and may then curve downwardly at an angle relative to the horizontal portion. More specifically, the and lower plate 30 may include a portion 30a that extends outwardly and generally perpendicularly with respect to the patient from the lower tooth guide 32. The lower plate 30 may also include a curved section 30b. The lower plate 30 may also include a descending portion 30c that extends from the curved portion. The curved portion 30b may form an angle of between about 120 degrees and about 165 degrees between the portion 30a and the descending portion 30c. This represents an angle of the descending portion 30c being between about 35 degrees and 75 degrees with respect to the patient. In one preferred embodiment, the curved section 30b may form an angle of between about 135 degrees and 158 degrees between the portion 30a and the descending portion 30c. This represents an angle of the descending portion 30c of between about 45 degrees and 68 degrees with respect to the patient. It will be appreciated that any suitable angle may be used. In another preferred embodiment, the curved section 30b may form an angle of about 158 degrees between the portion 30a and the descending portion 30c. This represents an angle of the descending portion 30c of about 68 degrees with respect to the patient. Further, it is preferred that the angle used for the upper plate 16 also be the angle used for the lower plate 30 so that when the AAD 10 is in the neutral position, as shown in FIG. 4a, the upper plate 16 and lower plate 30 are positioned adjacent each other.

The lower plate 30 has a plurality of teeth 36. The teeth 36 are preferably located in a position below the top surface of the lower plate 30. It will be appreciated, however, that the teeth 36 may extend above the top surface of the lower plate 30. The teeth 36 of the lower plate 30 cooperate with the pawl 38 on the upper plate 16 to form a ratchet mechanism. The teeth 36 and pawl 38 cooperate to allow the lower plate 30 to move downwardly and outwardly, from the perspective of the patient, relative to the upper plate 16 from a neutral position to an extended position and to become secured in any number of extended positions. More specifically and as best seen in FIG. 7, each tooth 36 has a generally flat surface 36a and a ramped or angled surface 36b. Similarly, the pawl 38 includes a generally flat surface 38a and a ramped or angled surface 38b. The generally flat surface 38a of the pawl 38 can engage the generally flat surface 36a of a tooth 36 to inhibit longitudinal movement of the lower plate 30 in one direction. The ramped surface 36b of the teeth 36 allows longitudinal movement of the lower plate 30 in one direction by engaging the ramped surface 38b and guiding the pawl 38 over the respective tooth 36. More specifically, as the lower plate 30 is moved outwardly and downwardly, away from the patient, in the direction of the arrows of FIGS. 4b and 8, the ramped surface 36b of each tooth 36 engages the ramped surface 38b of the pawl 38 to thereby guide the pawl 38 over the respective tooth 36. This allows the lower plate 30 to be moved outwardly and downwardly relative to the patient to simultaneously protrude and distract the lower jaw. Once the pawl 38 passes over the tooth 36, the pawl 38 descends and the flat surface 38a of the pawl 38 can engage the flat surface 36a of the tooth to inhibit movement of the lower plate 30 in the longitudinal direction toward the patient. In this way, a clinician can move the lower plate 30 to the desired extended position relative to the upper plate 16 and the ratchet mechanism will maintain the lower plate 30 in the desired extended position. It will be appreciated that any number of teeth 36 may be used and may be placed to allow any number of desired extended positions.

The lower AAD component 14 further includes a lower force receiving plate generally indicated at 40. In the embodiment shown, the lower force receiving plate 40 extends transversely to the lower plate 30 and is connected thereto. As shown, the lower force receiving plate 40 extends downwardly from the lower plate 30. The lower force receiving plate 40 may be generally curved as shown in the Figures. It will be appreciated, however, that the lower force receiving plate 40 may take any suitable geometric configuration. It will be appreciated that the lower force receiving plate 40 may be disposed at locations on the lower plate 30 other than at the end thereof.

The back side of the lower force receiving plate 40 may include an area or surface 42 that acts as a hard stop as the lower AAD component 14 is moved from an extended position to the neutral position. As shown in FIGS. 4a and 4b, the surface 42 may engage a portion of the leg 20a and leg 20b, not shown, to inhibit further movement of the lower AAD component 14 in a direction toward the patient. Such a hard stop may prevent the lower AAD component 14 from moving past the neutral position.

The lower tooth guide 32 may include an area or surface 44 that acts as a hard stop as the lower AAD component 14 is moved to a fully extended position. As shown in FIG. 4b, the surface 44 may engage a portion of the leg 20a and leg 20b, not shown, to inhibit further movement of the lower AAD component 14 in the direction away from the patient. Such a hard stop may prevent the lower AAD component 14 from moving outwardly to a fully extended position past a predetermined amount. This may reduce the ability of the lower AAD component 14 from moving too far and causing dislocation at the joint. In one preferred embodiment, the length of travel allowed between the hard stops may be about 22 mm. In a preferred embodiment the lower tooth AAD member 14 may extend downwardly and outwardly with respect to the patient and be sized to allow for distraction of the jaw of up to about 15 mm and allow for a protrusion of the jaw of up to about 15 mm. It will be appreciated that the lower AAD member 14 may extend any desirable distance. It is preferred to have the lower AAD member extend downwardly and outwardly up to an amount such that it provides the most positive effect on opening and maintaining the patient's airway, without dislocating the patient's mandible.

The lower AAD component 14 is preferably molded as a single piece. And as set forth above a relatively softer urethane material may be molded over, or otherwise placed over, the lower tooth guide 18. The lower AAD component 14 is preferably rigid.

As set forth above, the bottom side of the upper plate 16, legs 20a, 20b and lips 22a and 22b preferably cooperate to form a guide to receive a lower plate 30. More specifically, when the AAD 10 is assembled, the lower plate 30 is received in the space between the bottom side of the upper plate 16, the legs 20a and 20b and the lips 22a and 22b. When the AAD is assembled, the lower plate 30 is moveable in the longitudinal direction relative to the upper plate 16 within the guide or space formed between the bottom side of the upper plate 16, legs 20a, 20b and lips 22a and 22b.

The AAD may further include an oxygen delivery housing generally indicated at 46. The oxygen delivery housing may comprise an enclosure wall 48. The enclosure wall 48 provides a generally bowl shaped enclosure wall. The enclosure wall 48 is configured to provide a space 50 between the enclosure wall 48 and the upper plate 16 as best viewed in FIG. 5. The enclosure wall 48 preferably extends from the upper plate 16. The periphery of the enclosure wall 48 is preferably sealed to the upper plate 16 near the upper tooth guide 18. The enclosure wall 48 may extend from the portion 16a over the curved portion 16b and on the descending portion 16c of the upper plate 16 and create the space 50 therebetween. It will be appreciated, however, that the enclosure wall 48 may extend on less than all of these portions. The enclosure wall 48 may take any suitable configuration and should provide an adequate space 50 for allowing oxygen delivery.

The oxygen delivery housing 46 may further include a tubing connecting portion generally indicated at 52. The tubing connecting portion 52 includes a generally cylindrical section 54. The generally cylindrical section includes a fluid passageway 56 therethrough. The tubing connecting portion 52 extends from the enclosure wall 48. The fluid passageway 56 is in fluid communication with the space 50. The tubing connecting portion 52 may include a frustoconical section 58. The frustroconical section 58 may aid in retaining tubing 60 on the tubing connecting portion 52.

In a preferred embodiment, tubing 60 is positioned about the tube connecting portion 52. The tubing 60 may be positioned over the frustoconical section 58 to aid in retaining the tubing 60 on the connecting portion 52. The other end of the tubing may be connected to a fluid source, such as by way of non-limiting example, an oxygen supply source (not shown). The tubing may be used to deliver oxygen to the space 50 which oxygen will, in turn, be delivered in the proximity of the patient's mouth.

Figure 9:
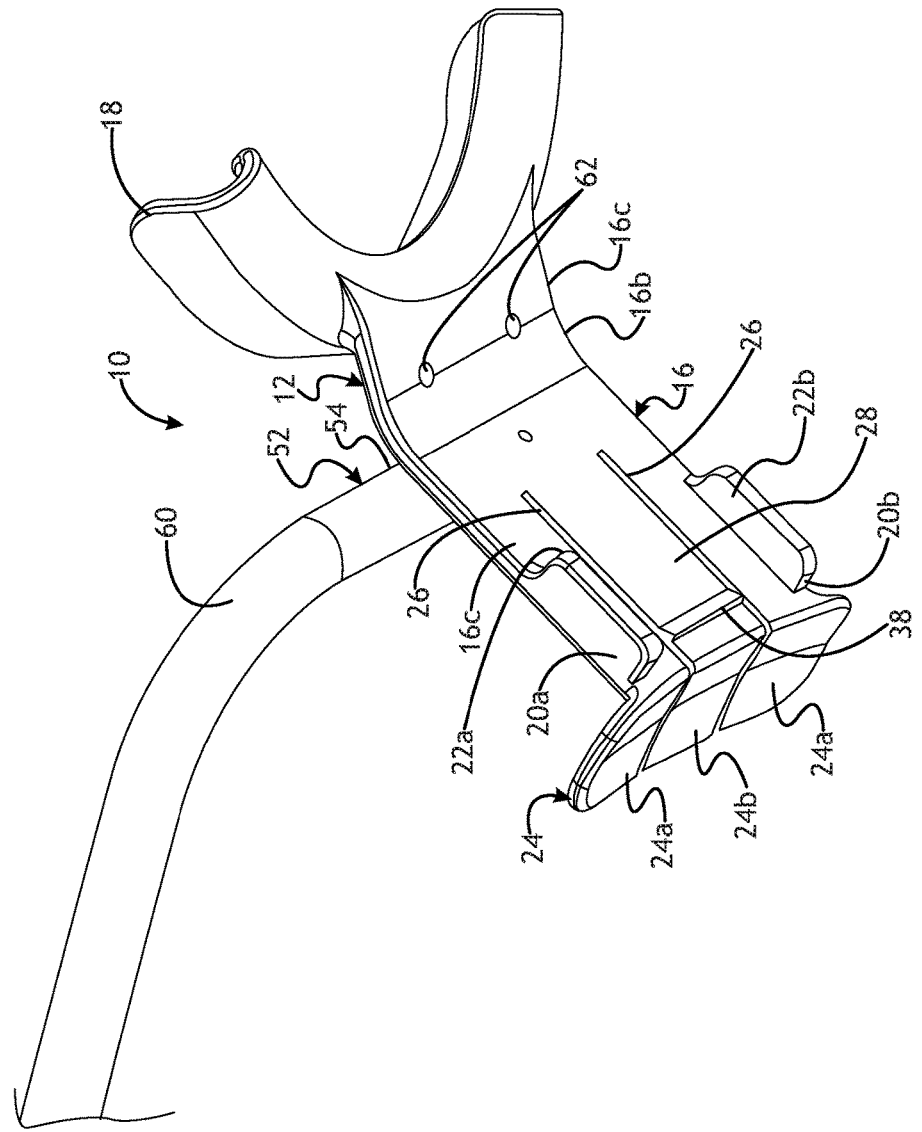
FIG. 9 is a perspective view of the upper AAD component of FIG. 1.

As best seen in FIG. 9, the upper plate 16 may include one or more openings 62 therethrough. The openings 62 are in positioned such that they are in an area beneath the space 50 provided by the enclosure wall 48. The openings 62 are in fluid communication with the space 50. It is most preferred that the openings 62 be positioned such that they near the section 16a or curved section 16b so that fluid, such as oxygen exiting therefrom is delivered in proximity to the patient's mouth. It will be appreciated, however, that the openings 62 can be positioned in any suitable location. Further, the openings 62 may have any desired size or shape. As shown, the openings 62 have a generally circular cross section. Further, while two openings 62 are shown, it will be appreciated that any number of openings may be used.

The enclosure wall 48 may include one or more legs 64, as best seen in FIG. 5. The legs 64 may be used to help secure the enclosure wall 48 with the upper plate 16. The upper plate 16 may include one or more openings 66 for receiving the legs 64. In order to secure the enclosure wall 48 with the upper plate 16, the legs 64 may be positioned within the openings 66. The legs 64 are inserted into the openings 66 until the periphery of the enclosure wall 48 engages the upper plate 16. In this way, the space 50 is created. The legs 64 may be friction fit within the openings 66. The legs 64 may also be heat staked to the openings 66. It will be appreciated that the legs 64 may additionally or alternatively be ultrasonically welded to the opening 66 or secured with an adhesive. It will further be appreciated that the legs 64 and openings 66 may not be necessary in alternate embodiments. For example, the periphery of the enclosure wall 48 may be secured directly to the upper plate 16 in any suitable manner. By way of non-limiting example, the enclosure wall 48 may be secured to the upper plate 16 by ultrasonic welding or the use of adhesives. Similarly, it may be possible to make the enclosure wall 48 as a unitary piece with the upper plate 16. It is preferred that the enclosure wall 48 be secured to the upper plate 16 in such a manner that it is sealed thereto to restrict, and preferably prohibit fluid from flowing between the enclosure wall 48 and the upper plate 16.

Figure 10:
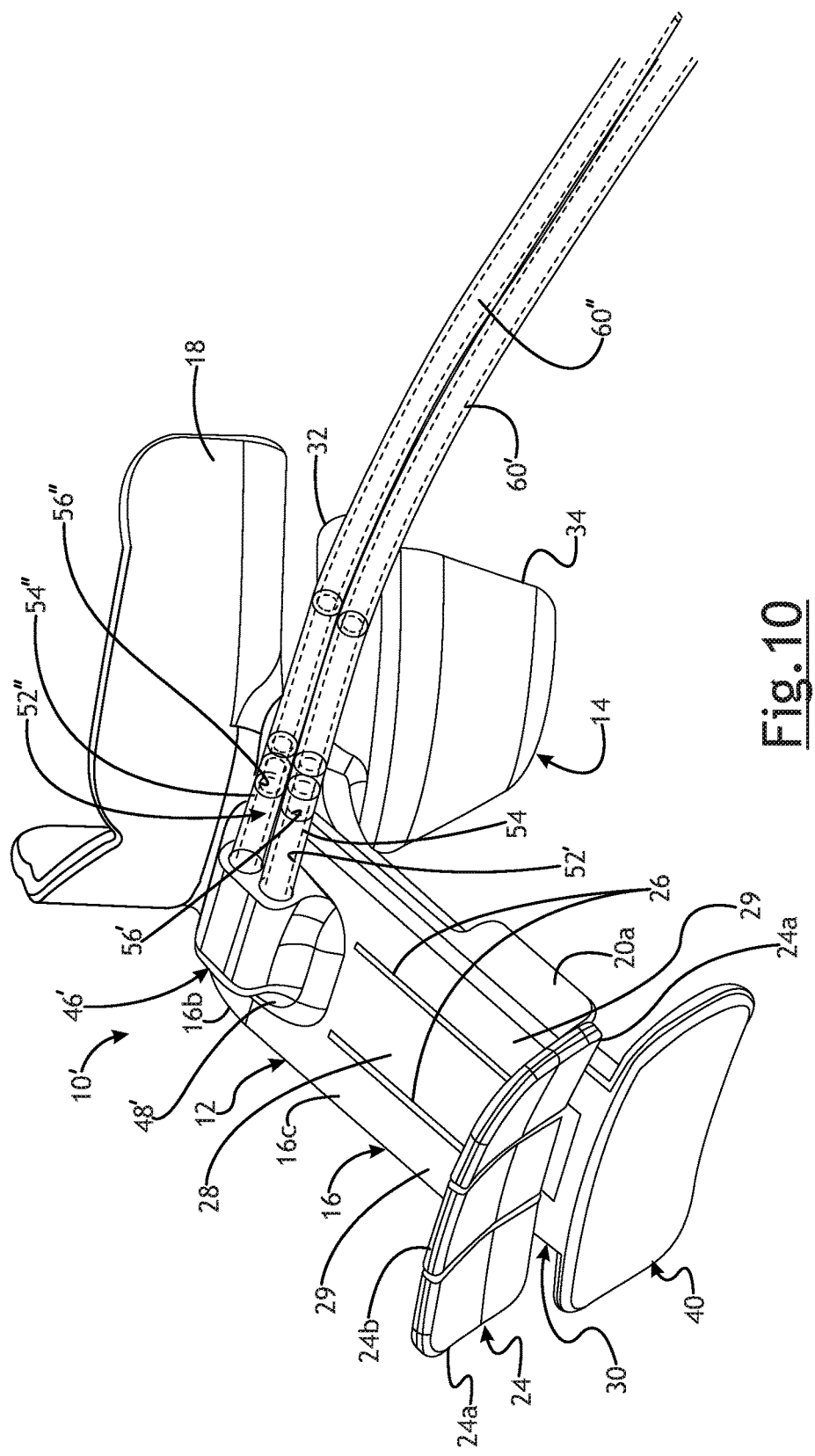
FIG. 10 is a perspective view of an alternate embodiment.
Figure 11:
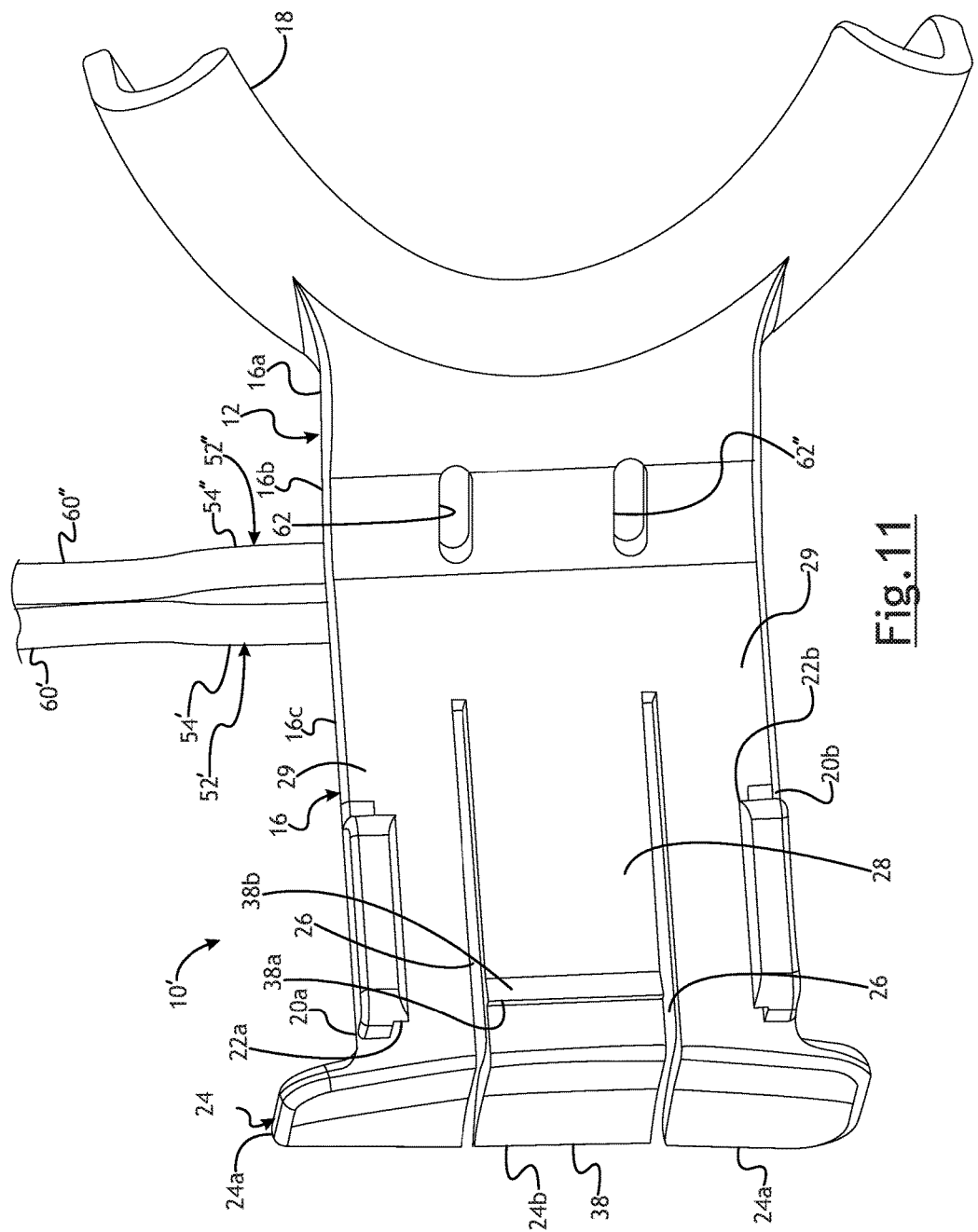
FIG. 11 is a bottom view of an upper AAD component of the embodiment of FIG. 10.
Figure 12:
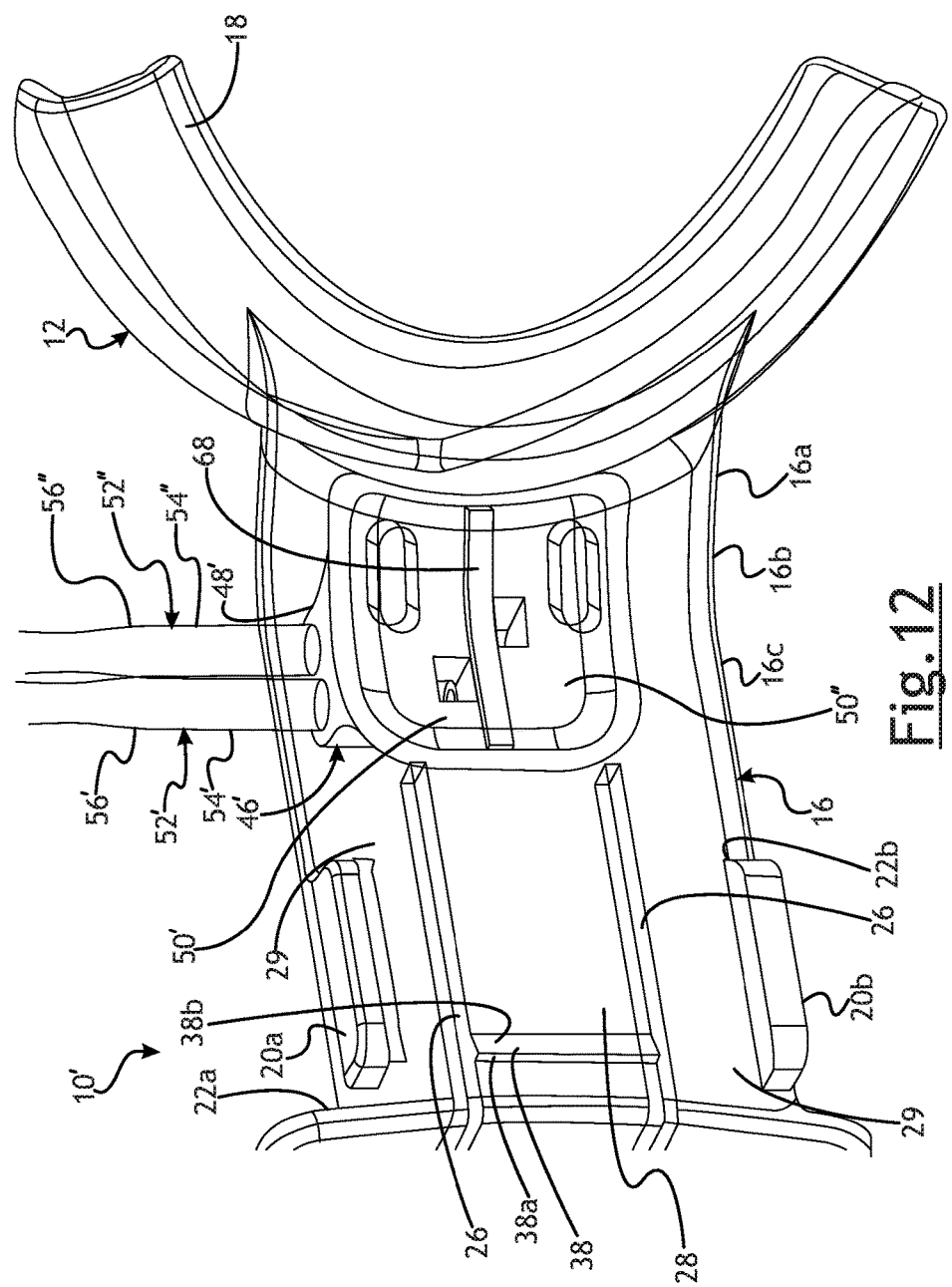
FIG. 12 is a bottom view of an upper AAD component of the embodiment of FIG. 10 partially broken away also showing the partitioned oxygen delivery and carbon dioxide housing.

An alternate embodiment of the AAD 10' is shown in FIGS. 10-12. In this alternate embodiment, the components of the AAD 10' are the same as those of the AAD 10 of FIGS. 1-9, with the exception of modifications to the oxygen delivery housing 46' in this embodiment, and the other slight differences discussed below. The oxygen delivery housing 46' includes an enclosure wall 48'. A septum 68 may extend from the enclosure wall 48' to the upper plate 16 to create two separate spaces 50', 50" as best seen in FIG. 12.

The oxygen delivery housing 46' may further include one or more tubing connecting portions generally indicated at 52', 52". The tubing connecting portions 52', 52" include a generally cylindrical section 54', 54" respectively. The generally cylindrical sections 54', 54" include a fluid passageway 56', 56" therethrough. The tubing connecting portions 52', 52" extend from the enclosure wall 48'. The fluid passageways 56', 56" are in fluid communication with the spaces 50' and 50" as best shown in FIG. 12. The tubing connecting portions 52', 52" may include a frustoconical section (not shown) as described in connection with the embodiment of FIGS. 1-9.

In the embodiment of FIGS. 10-11, two separate tubing connecting portions 52', 52" are used to connect with two different sets of tubing 60', 60", respectively. In this embodiment, one of the tubing 60' is connected to a fluid source, such as an oxygen supply source and is used to deliver fluid, preferably oxygen, to the space 50' as best seen in FIG. 12. The upper plate 16 includes an opening 62' therethrough in fluid communication with the space 50'. This allows fluid such as oxygen to be delivered through the opening 62' in the proximity of the patient's mouth, as described above. The opening 62' may be elongated to allow sufficient oxygen to be delivered to the patient. It will be appreciated that the opening 62' may take any suitable size and shape and may be located in any suitable location on the upper plate 16. Further, any number of openings 62' may be used.

The upper plate 16 further includes a second opening 62" therethrough in fluid communication with the space 50". This separate space 50" is in fluid communication with the associated passageway 56" and tubing 60" which may be use to convey the patient's exhaled gasses to monitor the patient's end-tidal carbon dioxide wave form and respiratory rate. The tubing 62" may be connected to a carbon dioxide monitoring system (not shown). The opening 62" may be elongated to allow sufficient exhaled air containing carbon dioxide to be delivered from the patient to be monitored. It will be appreciated that the opening 62" may take any suitable size and shape and may be located in any suitable location on the upper plate 16. Further, any number of openings 62" may be used.

The enclosure wall 48' and septum 60 are preferably secured to the upper plate 16 in any suitable manner. By way of non-limiting example, the enclosure wall 48' and septum 60 may be secured to the upper plate 16 by ultrasonic welding or the use of adhesives. Similarly, it may be possible to make the enclosure wall 48' with the septum 60 as a unitary piece with the upper plate 16. It is preferred that the enclosure wall 48' be secured to the upper plate 16 in such a manner that it is sealed thereto to restrict, and more preferably prohibit fluid from flowing between the enclosure wall 48' and the upper plate 16. It is further preferred that the septum 60 be secured to the upper plate 16 and sealed thereto to restrict and more preferably to prevent fluid from flowing past the septum. This will create the two spaces 50', 50" which preferably are not in fluid communication with each other.

To assemble the AAD 10, 10', the oxygen delivery housing 46, 46' is first secured to the upper plate 16 as described above. The upper AAD component 12 is positioned over the lower AAD component 14 as shown in FIG. 3. The upper plate 16 may be aligned over the lower plate 30. The upper plate 16 and lower plate 30 are moved toward each other as indicated by the arrows in FIG. 3. The lower plate 30 may contact the ramped surfaces of the lips 22a and 22b on the legs 20a and 20b, respectively. As the upper plate 16 and lower plate 30 continue to move toward each other, the legs 20a and 20b flex outwardly relative to the axial direction of the upper plate 16. This allows the upper plate 16 to be positioned adjacent to the lower plate 30. Once the lower plate 30 has moved past the lips 22a, 22b, the legs 20a, 20b return to their unflexed position. In this position, the lower plate 30 is retained in the guide or space that is defined by the bottom side of the upper plate 16, legs 20a, 20b and lips 22a and 22b. The pawl 38 may engage one of the teeth 32 in the lower plate 30. It is preferred that when the AAD 10, 10' is assembled, the upper tooth guide 18 and lower tooth guard 32 are positioned adjacent each other as best seen in FIG. 4a. This may be referred to as the neutral or non-extended position.

Figure 8:
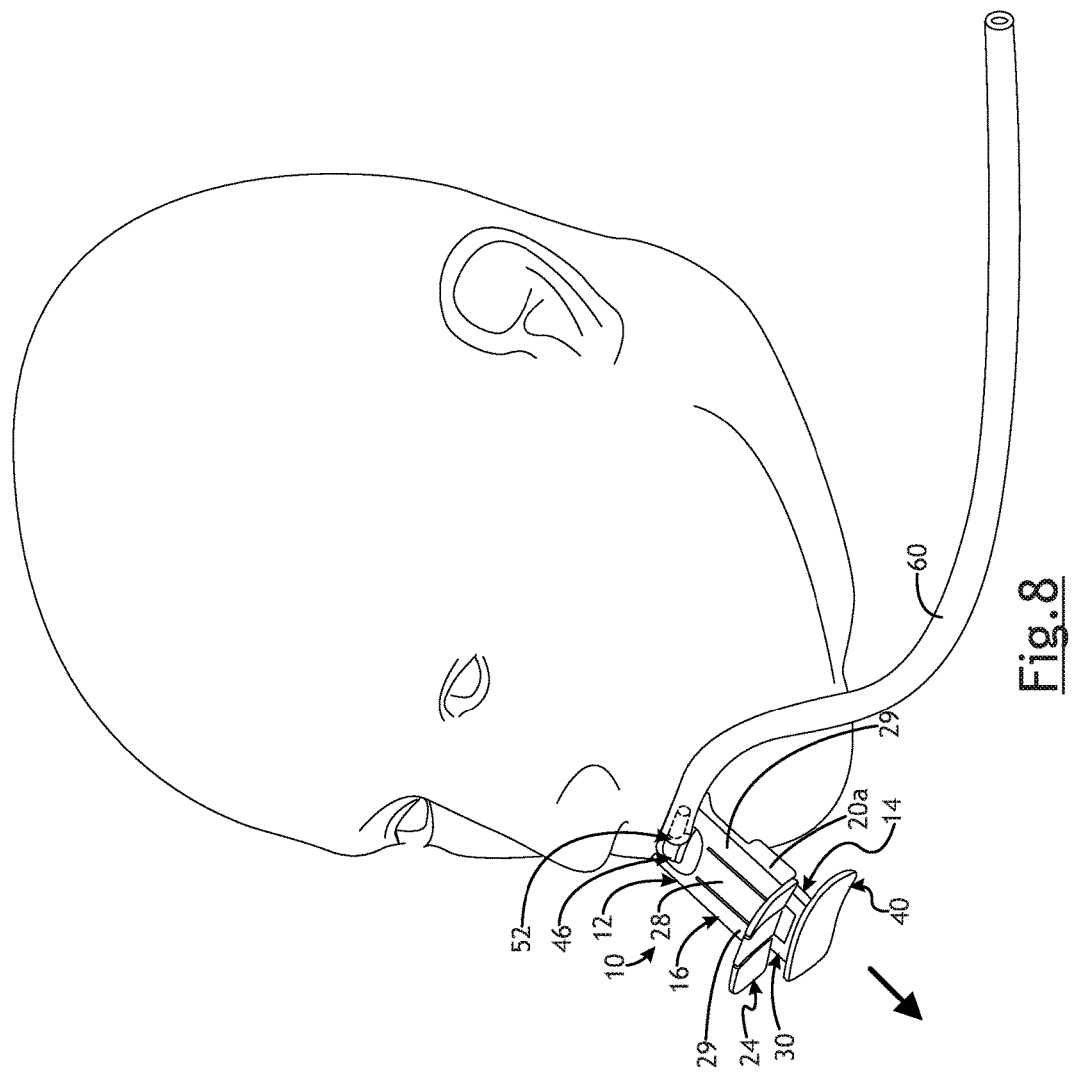
FIG. 8 is a perspective view of the embodiment of FIG. 1 as used.

In order to use the AAD 10, 10' to open and maintain a patient's airway, the assembled AAD 10, 10', in the neutral position, is positioned relative to a patient, as shown in FIG. 4a. The upper tooth guide 18 is positioned to envelope a dentate or edentulous alveolar ridge of the patient. The lower tooth guide 32 is positioned in such a way the dental guard 34 extends to the lingual aspect of the patient's mandible. By using an upper tooth guide 18 and a lower tooth guide 32 as set forth, the AAD 10, 10' can be used with a dentate or non-dentate application with a variety of dental arch shapes. It will be appreciated that in some instances it may be necessary to place the AAD 10, 10' in an extended position prior to positioning the AAD 10, 10' relative to the patient. Once the AAD 10, 10' is positioned relative to the patient, the patient's mandible can be distracted and protruded as follows. A clinician, such as a surgeon, can place his thumbs on the distal surfaces of outermost sections 24a (those furthest away from the patient) of the upper force receiving plate 24. The clinician can place his index or other fingers on the back side (closest to the patient) of the lower force receiving plate 40. The clinician can hold his thumbs in the same position relative to the patient in such a way that the upper AAD component 12 remains in a relatively fixed position relative to the patient. The clinician can apply a force to the lower force receiving plate in a direction downwardly and away from the patient, as shown by the arrows in FIGS. 4b and 8. By applying such a force, the lower AAD component 14 moves downwardly and away from the patient to an extended position, as best seen in FIGS. 4b and 8. The ratchet mechanism, pawl 38 and teeth 36, allow movement of the lower AAD component 14 downwardly and outwardly away from the patient while inhibiting movement in the opposite direction. Because there are several teeth 36, the clinician can extend lower AAD component to any desired extended position along the distraction path relative to the upper AAD component 12. This allows for relatively smooth mandibular distraction while minimizing any torque. This movement helps maintain an open airway for the patient.

The length of travel of the lower AAD component 14 relative to the upper AAD component may be limited by the hard stop, the area 44 on the lower AAD component engaging the legs 20a, 20b of the upper AAD component 12. By providing a hard stop, the length of travel of the lower AAD component 14 relative to the upper AAD component can be controlled. This may help inhibit dislocation of the mandibular joint. In one embodiment, the lower AAD component 14 may extend up to about 22 mm before the hard stop occurs when the surface 44 engages the legs 20a, 20b to inhibit further extension of the lower AAD component 14 relative to the upper AAD component 12.

Oxygen may be delivered to the patient through the AAD 10, 10'. Tubing 60, 60' may be connected to an oxygen supply source (not shown). The tubing 60, 60' is also connected to the generally cylindrical section 54, 54'. Oxygen can then be supplied to the tubing 60, 60' which, in turn flows through the fluid passageway 56, 56' into the space 50, 50'. The oxygen then flows out the openings 62, 62' for delivery to the patient.

Additionally, the end-tidal carbon dioxide wave form and respiratory rate of the patient may be monitored. The tubing 60" may be connected to a carbon dioxide monitoring system (not shown). The tubing 60" is also connected to the generally cylindrical section 54". As the patient breathes out, the exhale gasses are supplied to the space 50" through the opening 62". The gasses then flow through the fluid passageway 56" into the tubing 62" and to the carbon dioxide monitoring system. While it is described that the patient's end-tidal carbon dioxide may be monitored, it will be appreciated that any exhaled gases from the patient may be monitored in this way.

Once the need for the AAD 10, 10' ends, the AAD 10, 10' can be returned to the neutral position. This may be done by the clinician applying an upward force to the center section 24b of the upper force receiving plate 24. As best seen in FIG. 7, the center section 24b can be raised sufficiently to raise the center section 28 of the upper plate 16 to disengage the pawl 38 from the teeth 36 of the lower plate 30. Once the pawl 38 is disengaged from the teeth 36, the lower AAD component 14 can return to the neutral position. A hard stop, surface 42, on the lower force receiving plate 40 engaging the legs 20a, 20b of the upper AAD component 12, inhibits movement of the lower AAD component 14 past the neutral position. Upon returning the AAD 10, 10' to the neutral position, the clinician may then remove the AAD 10 10' from the patient.

Figure 20:
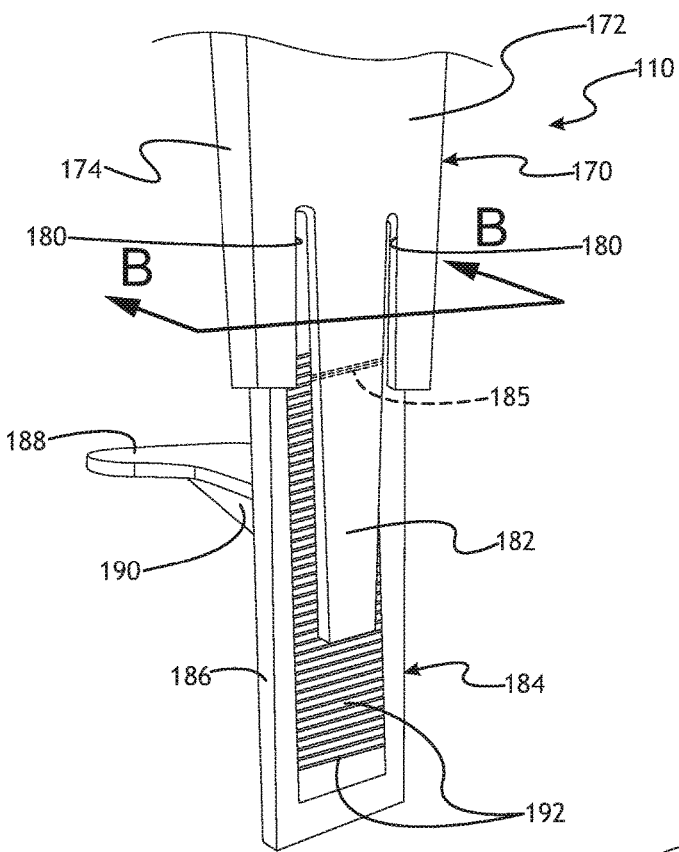
FIG. 20 a perspective view partially broken away of the embodiment of FIG. 13.
Figure 21:
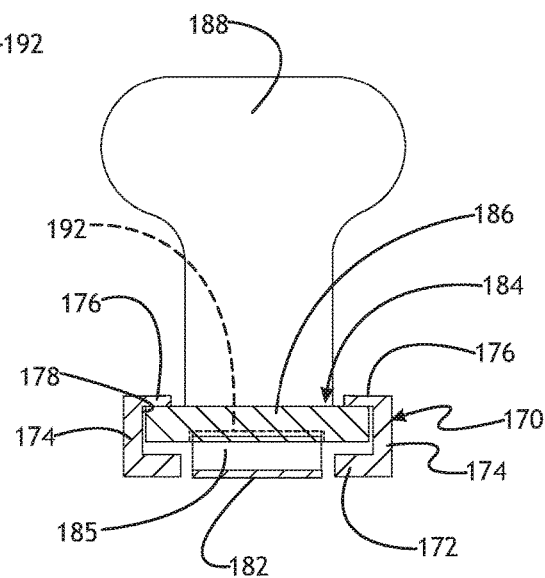
FIG. 21 is a cross sectional view taken along lines B-B of FIG. 20.
Figure 22:
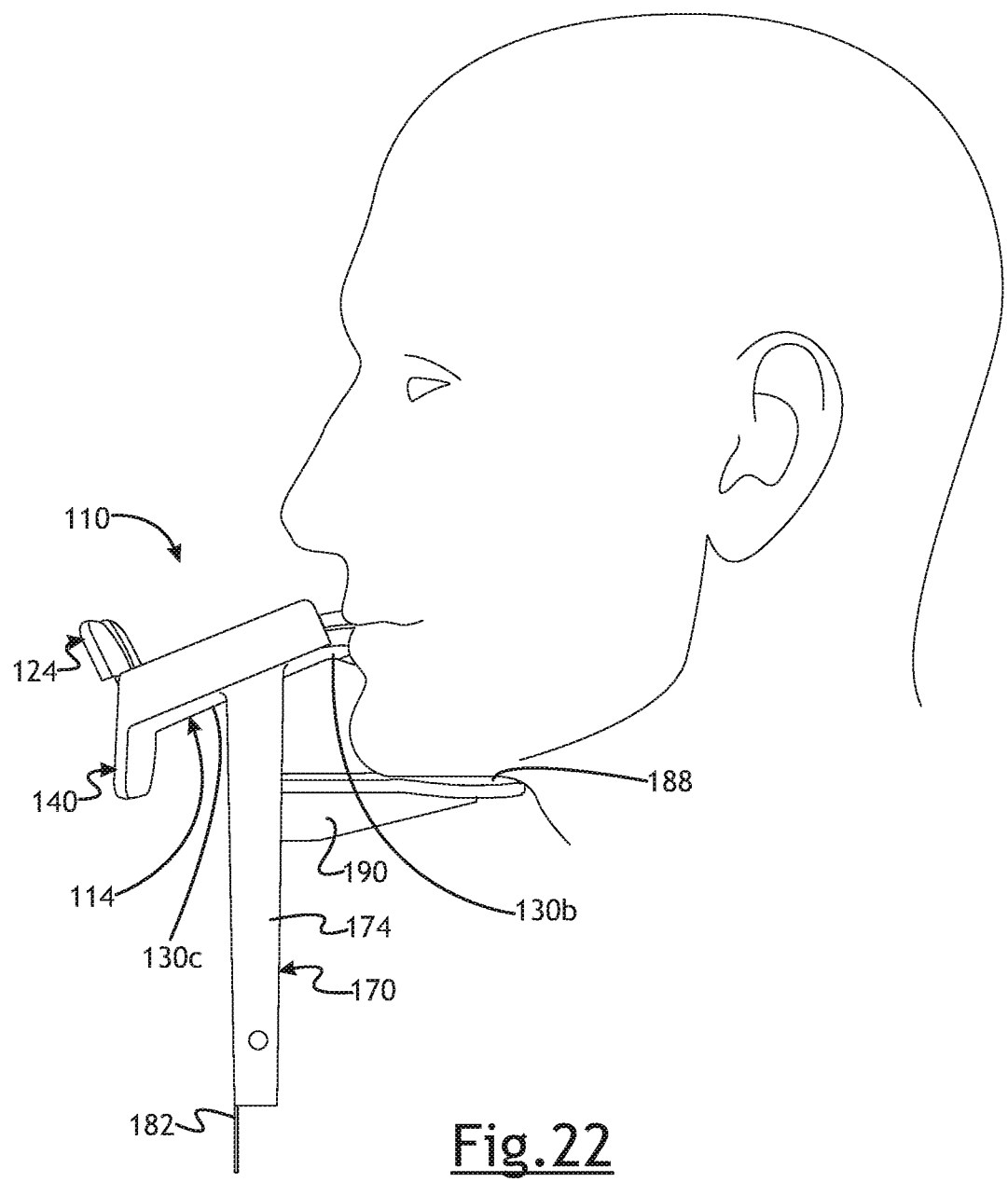
FIG. 22 is a perspective view of the embodiment of FIG. 13 positioned on a patient.

FIGS. 13-22 show an alternate embodiment of the present invention. In general, the embodiment of FIGS. 13-22 adds the ability to stabilize the AAD relative to a patient by further engaging a portion of the AAD to a patient's chin, as best seen in FIG. 22. The other structure of the AAD is similar to the structure of the embodiments discussed above with the same modifications as specifically discussed below. Like numerals, offset by 100 will be used to identify similar structure.

Figure 13:
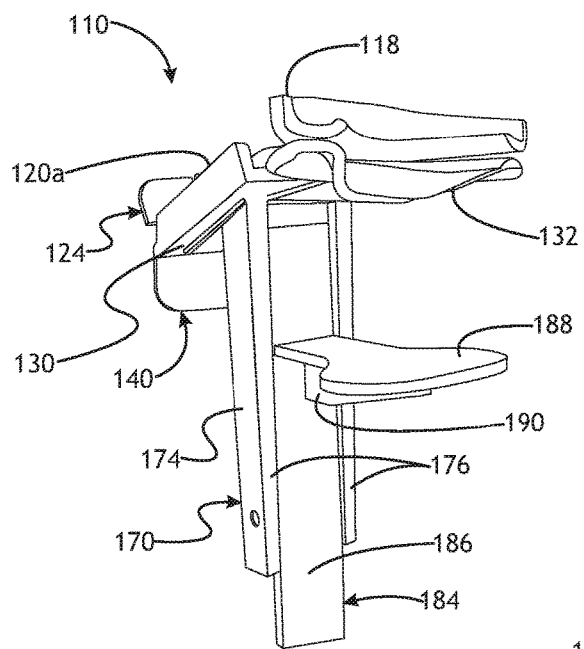
FIG. 13 is a perspective view of an alternate embodiment showing a chin support in a non-extended position.
Figure 14:
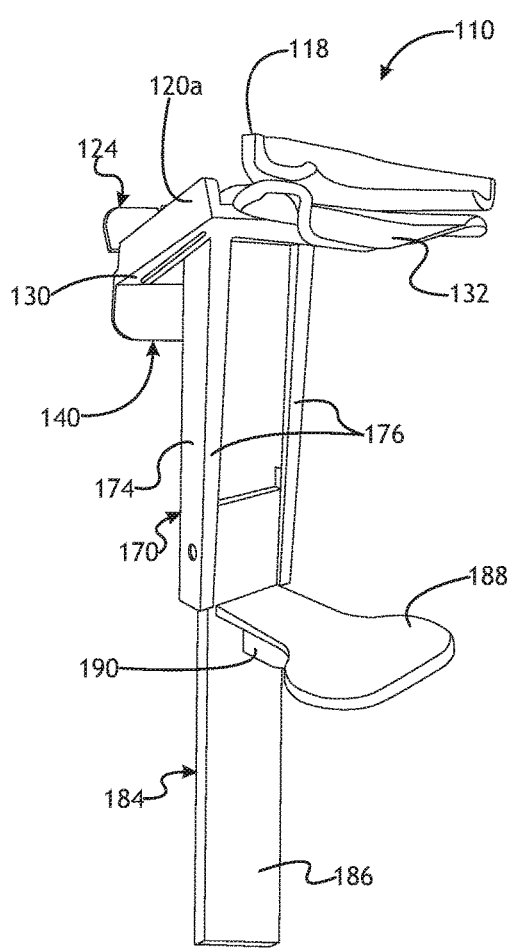
FIG. 14 is a perspective view of the embodiment of FIG. 13 showing a chin support in an extended position.
Figure 15:
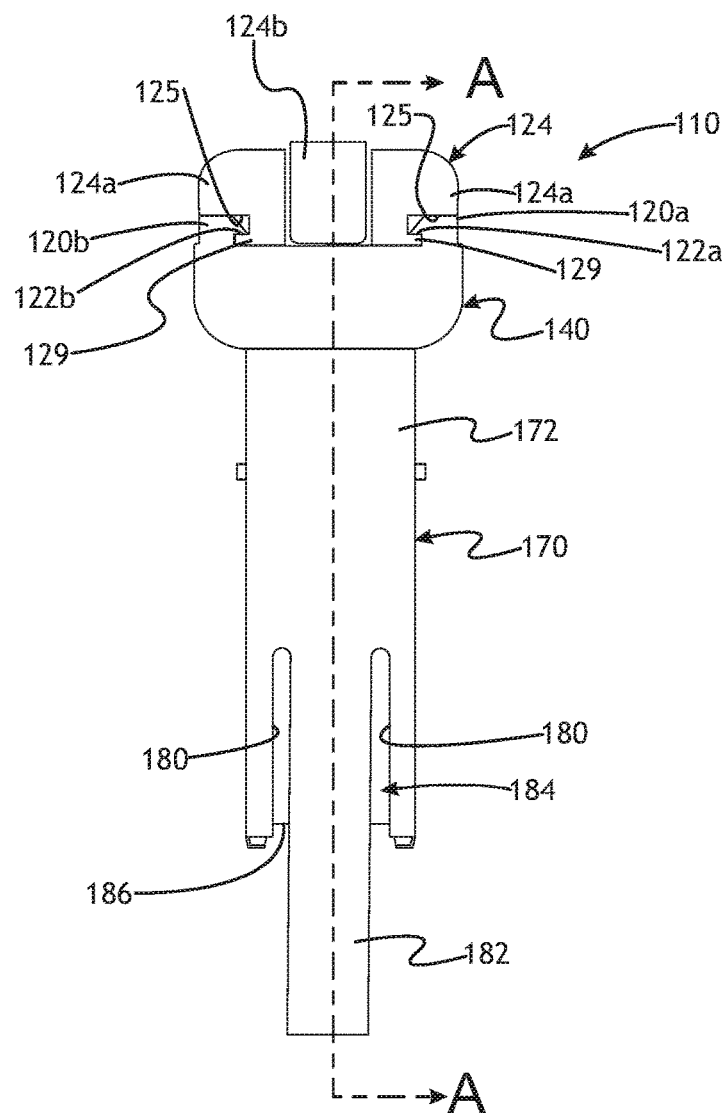
FIG. 15 is a front view of the embodiment of FIG. 13.

An embodiment of an airway assist device (AAD) is generally shown at 110 in FIGS. 13-22. The AAD 110 may be useful to allow for lower jaw protrusion and distraction that opens the posterior airway (PAW) space and may also allow for supplemental oxygen delivery. As best shown in FIG. 15, the AAD 110 may comprise a first or upper AAD component generally indicated at 112 and a second or lower AAD component, generally indicated at 114. The upper AAD component 112 may comprise an injection molded component. The lower AAD component 114 may comprise an injection molded component. The upper AAD component 112 and lower AAD component 114 may comprise any suitable material.

In the embodiment shown, the upper AAD component 112 has an upper plate generally indicated at 116. The upper plate 116 is preferably connected to an upper tooth guide 118. The upper tooth guide 118 preferably envelopes a dentate or edentulous alveolar ridge of the patient. All or part of the upper tooth guide 118 may be covered with a relatively soft material. By way of non-limiting example, the upper tooth guide 118 may be overmolded with a relatively soft urethane material.

As shown, the upper plate 116 extends from the upper tooth guide 118. The upper plate 116 is preferably generally rectangular when viewed from the top. The upper plate 116 preferably extends downwardly and outwardly from the upper tooth guide 118. The upper plate 116 therefore may extend downwardly, in the direction of the patient's chin, and outwardly, away from the patient's face. While the upper plate 116 is described as being generally rectangular, it will be appreciated that the upper plate 116 may take any suitable geometrical configuration.

Figure 16:
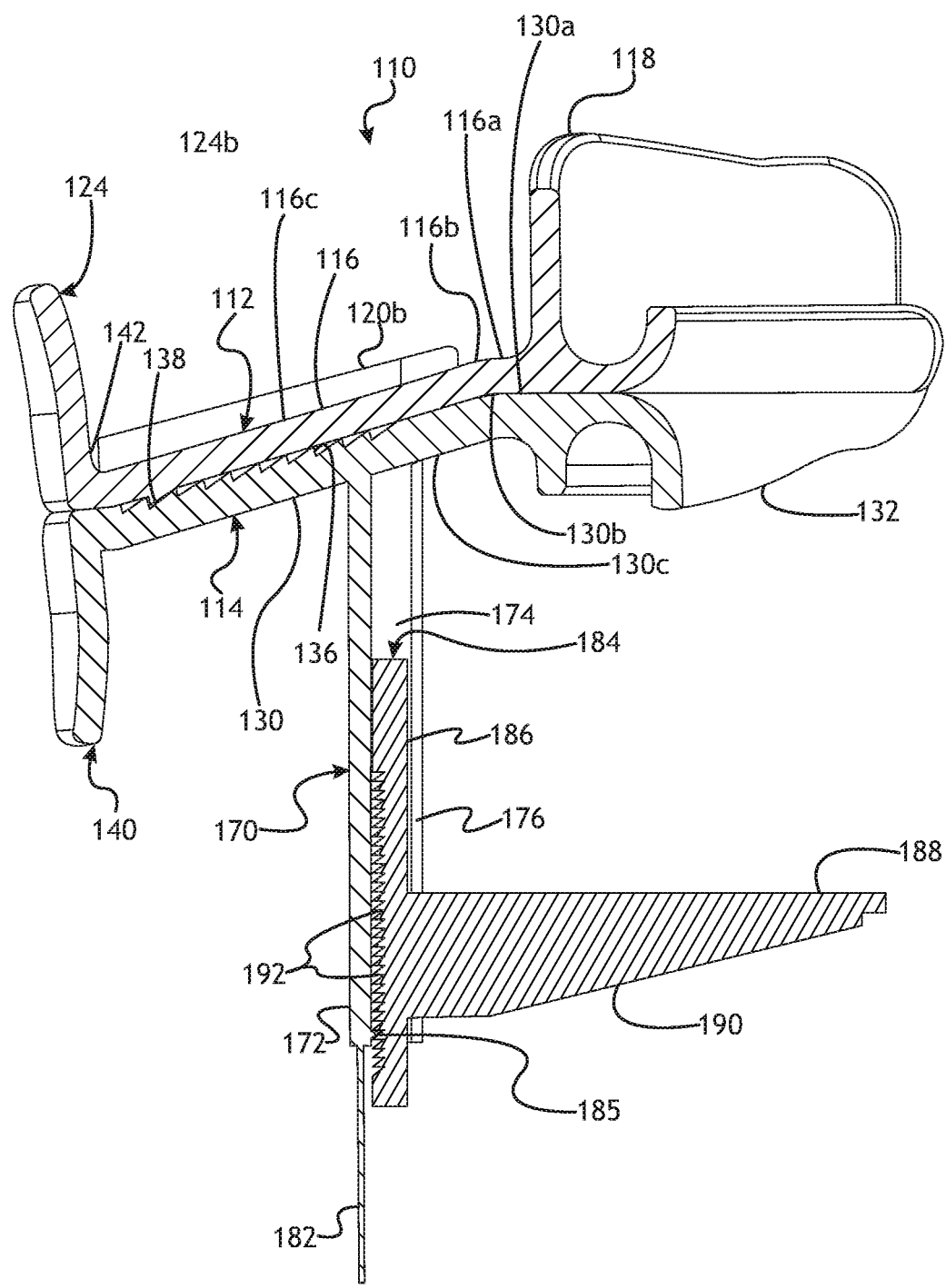
FIG. 16 is a cross sectional view taken along lines A-A of FIG. 15.

As shown in FIG. 16, the upper plate 116 may be curved when viewed from the side. That is, the upper plate may extend horizontally from the upper tooth guide 118 and may then curve downwardly at an angle relative to the horizontal portion. More specifically, the upper plate 116 may include a portion 116a that extends outwardly and generally perpendicularly with respect to the patient from the upper tooth guide 118. The upper plate 116 may also include a curved portion 116b. The upper plate 116 may also include a descending portion 116c that extends from the curved portion 116b. The curved portion 116b may form an angle of between about 120 degrees and about 165 degrees between the portion 116a and the descending portion 116c. This represents an angle of the descending portion 116c being between about 35 degrees and 75 degrees with respect to the patient. In one preferred embodiment, the curved section 116b may form an angle of between about 135 degrees and 158 degrees between the portion 116a and the descending portion 116c. This represents an angle of the descending portion 116c of between about 45 degrees and 68 degrees with respect to the patient. In another preferred embodiment, the curved section 116b may form an angle of about 158 degrees between the portion 116a and the descending portion 116c. This represents an angle of the descending portion 116c of about 68 degrees with respect to the patient. It will be appreciated that any suitable angle may be used.

Figure 17:
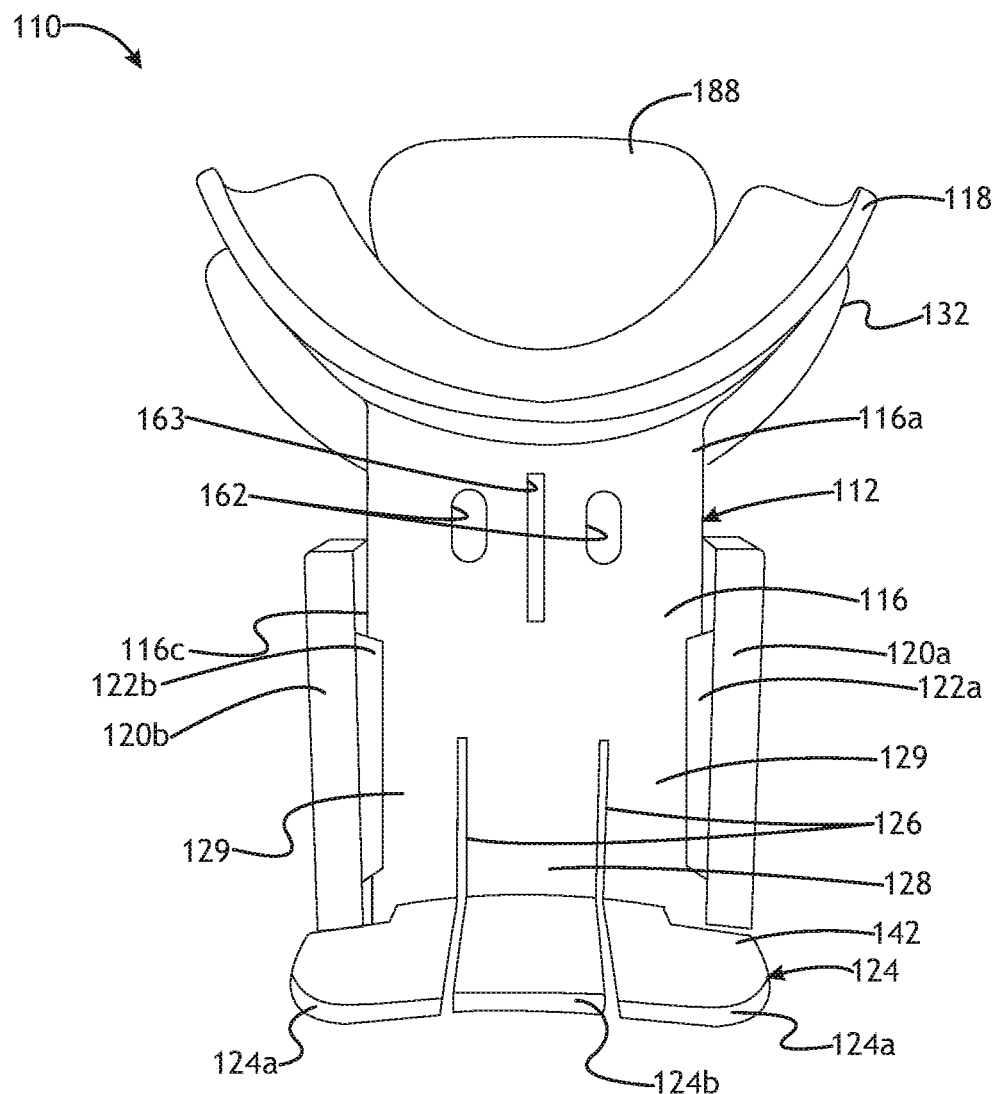
FIG. 17 is a top view of embodiment of FIG. 13.

As best seen in FIG. 17, the upper plate 116 includes a pair of spaced apart slits 126. A center portion 128 of the upper plate 116 is thereby formed between the slits 126. Outer portions 129 of the upper plate are adjacent the slits 26. The center portion 128 may flex relative to the outer portions 129 of the upper plate 116 in the vertical direction.

As best seen in FIG. 17, the center portion 128 of the upper plate 116 further includes a pawl 138 extending from the bottom surface thereof. The pawl 138 is part of a ratchet mechanism that is used to maintain the AAD 110 in an appropriate extended position, as will be described in more detail below.

The upper AAD component 112 further includes an upper force receiving plate generally indicated at 124. In the embodiment shown, the upper force receiving plate 124 extends transversely and preferably perpendicularly to the upper plate 116 and is connected thereto. As shown, the upper force receiving plate 124 extends upwardly from the upper plate 116. The upper force receiving plate 124 may be generally curved as shown in the Figures. It will be appreciated, however, that the upper force receiving plate 124 may take any suitable geometric configuration. In certain embodiments, the upper force receiving plate 214 may even constitute the end of the upper plate 116 without any upstanding portion. It will further be appreciated that the upper force receiving plate 124 may be disposed at locations on the upper plate 116 other than at the end thereof.

The upper force receiving plate 124 is preferably divided into a plurality of sections; two outermost sections 124a and a center section 124b. As shown in FIG. 17, the slits 126 are preferably contiguous from the upper plate 116 and onto the upper force receiving plate 124. Each of the sections 124a is preferably secured to the outer portions 129 of the upper plate 116. The center section 124b is preferably secured to the center portion 128 of the upper plate 116. In an embodiment as shown, the outermost sections 124a and center section 124b are integrally formed with the outer portions 129 and center portion 128, respectively of the upper plate 116. The center section 124b can flex in the direction away from the lower plate 130 relative to the outermost sections 124a and along with the center portion 128 of the upper plate 116. Further, outermost sections 124a may each define a passageway 125 therethrough to allow relative movement between the upper plate 116 and lower plate 130.

The upper AAD component 112 is preferably molded as a single piece. And as set forth above a relatively softer urethane material may be molded over, or otherwise placed over, the upper tooth guide 118. The upper AAD component 112 is preferably rigid. It will be appreciated, however that the center portion 128 and center section 124b can flex relative to the outer portions 129 of the upper plate 116 and the outermost sections 124a of the upper force receiving plate 124, respectively.

In the embodiment shown in FIGS. 13-22, the lower AAD component 114 has a lower plate generally indicated at 130. The lower plate 130 is preferably connected to a lower tooth guide 132. The lower tooth guide 132 further may include a lower dental guard 134 that extends such that it may engage the lingual aspect of the mandible of a patient. All or part of the lower tooth guide 132 and dental guard 134 may be covered with a relatively soft material. By way of non-limiting example, the lower tooth guide 132 and/or the lower dental guard 134 may be overmolded with a relatively soft urethane material.

As best seen in FIG. 16, the lower plate 130 extends from the lower tooth guide 132. The lower plate 130 preferably extends downwardly and outwardly from the lower tooth guide 132. The lower plate 130 therefore may extend downwardly, in the direction of the patient's chin, and outwardly, away from the patient's face. The lower plate 130 is preferably generally rectangular. While the lower plate 130 is described as being generally rectangular, it will be appreciated that the lower plate 130 may take any suitable geometrical configuration. As shown in FIG. 16, the lower plate 130 may be curved when viewed from the side. That is, the lower plate 130 may extend horizontally from the lower tooth guide 132 and may then curve downwardly at an angle relative to the horizontal portion. More specifically, the and lower plate 130 may include a portion 130a that extends outwardly and generally perpendicularly with respect to the patient from the lower tooth guide 132. The lower plate 130 may also include a curved section 130b. The lower plate 130 may also include a descending portion 130c that extends from the curved portion 130b. The curved portion 130b may form an angle of between about 120 degrees and about 165 degrees between the portion 130a and the descending portion 130c. This represents an angle of the descending portion 130c being between about 35 degrees and 75 degrees with respect to the patient. In one preferred embodiment, the curved section 130b may form an angle of between about 135 degrees and 158 degrees between the portion 130a and the descending portion 130c. This represents an angle of the descending portion 130c of about 45 degrees to about 68 degrees with respect to the patient. In another preferred embodiment, the curved section 130b may form an angle of about 158 degrees between the portion 130a and the descending portion 130c. This represents an angle of the descending portion 130c of about 68 degrees with respect to the patient. It will be appreciated that any suitable angle may be used. Further, it is preferred that the angle used for the upper plate 116 also be the angle used for the lower plate 130 so that when the AAD 110 is in the neutral position, as shown in FIG. 18, the upper plate 116 and lower plate 130 are positioned adjacent each other.

Figures 18, 19:
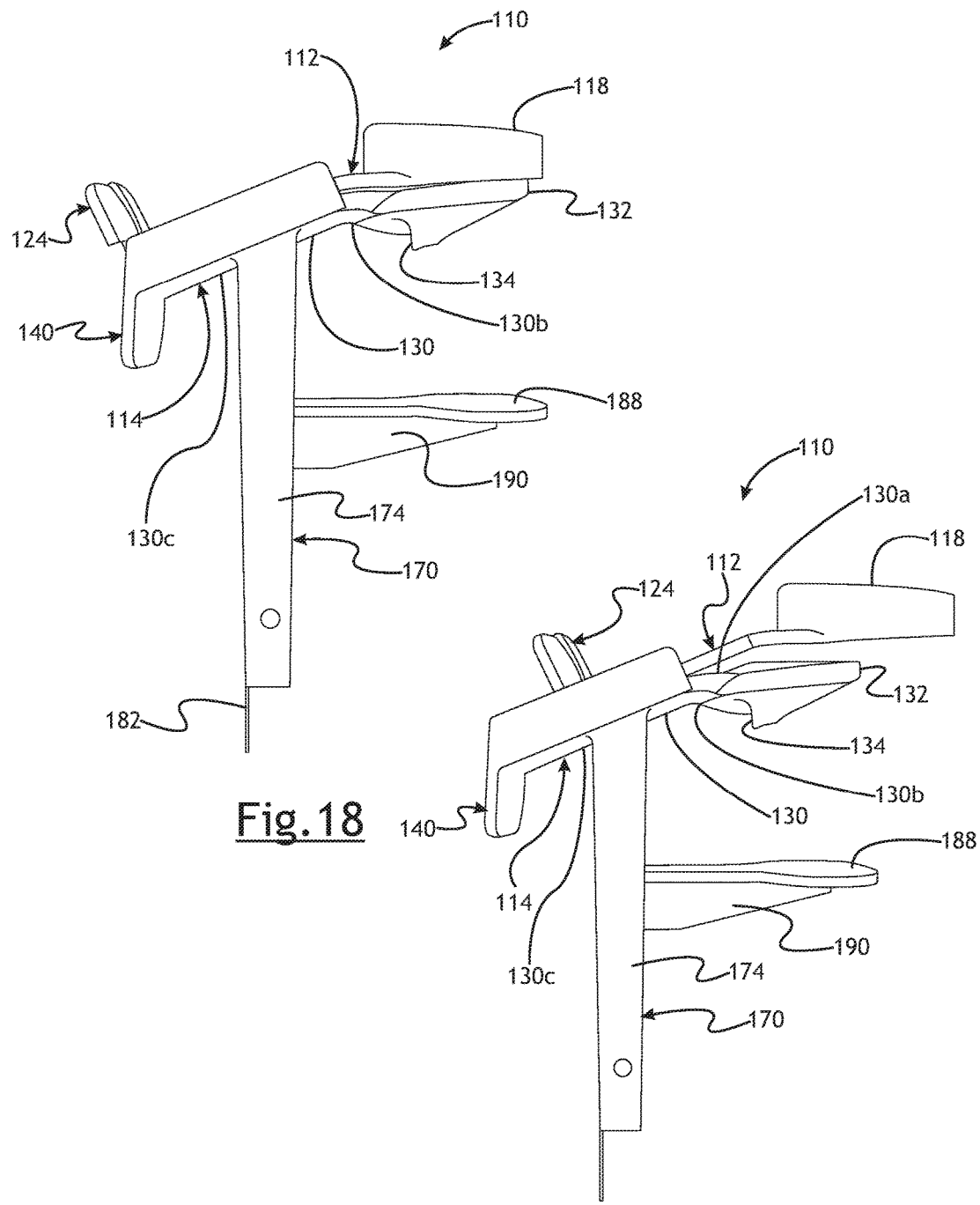
FIG. 18 is a side view of the embodiment of FIG. 13 in a neutral position.
FIG. 19 is a side view of the embodiment of FIG. 13 in an extended position.

As best seen in FIGS. 13, 17 and 18, the upper plate 16 preferably includes a pair of upstanding legs 120a, 120b. Preferably, the legs 120a and 120b are similarly constructed. The legs 120a, 120b extend upwardly from opposite sides of the upper plate 116. Each leg 120a, 120b has a lip 122a, 122b extending therefrom respectively. Each lip 122a and 12b extends in a direction inwardly or toward the direction of the centerline of the upper plate 116. The lower surfaces of each lip 122a and 122b are preferably generally rectangular and are preferably relatively smooth and parallel with the top surface of the lower plate 130. The upper surfaces of each lip 122a and 122b may be angled or ramped. The upper side of the lower plate 130, legs 120a, 120b and lips 122a and 122b preferably cooperate to form a guide to receive the upper plate 116, as will be described in more detail below.

The lower AAD component 114 further includes a lower force receiving plate generally indicated at 140. As shown in FIG. 16, the lower force receiving plate 140 extends transversely to the lower plate 130 and is connected thereto. As shown, the lower force receiving plate 140 extends downwardly from the lower plate 130. The lower force receiving plate 140 may be generally curved. It will be appreciated, however, that the lower force receiving plate 140 may take any suitable geometric configuration. It will be appreciated that the lower force receiving plate 140 may be disposed at locations on the lower plate 130 other than at the end thereof.

As with the embodiments described above, the lower plate 130 has a plurality of teeth 136 as best seen in FIG. 16. The teeth 136 are preferably located in a position below the top surface of the lower plate 130. It will be appreciated, however, that the teeth 136 may extend above the top surface of the lower plate 130. The teeth 136 of the lower plate 130 cooperate with the pawl 138 on the upper plate 116 to form a ratchet mechanism. The teeth 136 and pawl 138 cooperate to allow the lower plate 30 to move downwardly and outwardly, from the perspective of the patient, relative to the upper plate 16 from a neutral position to an extended position and to become secured in any number of extended positions, in the same manner as discussed above in connection with the other embodiments. This allows the lower plate 30 to be moved outwardly and downwardly relative to the patient to simultaneously protrude and distract the lower jaw. Once the pawl 138 passes over the tooth 136, the pawl 138 descends to engage the tooth 138 to inhibit movement of the lower plate 30 in the longitudinal direction toward the patient. In this way, a clinician can move the lower plate 130 to the desired extended position relative to the upper plate 116 and the ratchet mechanism will maintain the lower plate 130 in the desired extended position. It will be appreciated that any number of teeth 136 may be used and may be placed to allow any number of desired extended positions.

In one preferred embodiment, the preferred length of travel of the lower AAD member 114 relative to the upper AAD member 112 may be about 22 mm. In a preferred embodiment the lower AAD member may extend downwardly and outwardly with respect to the patient and be sized to allow for distraction of the jaw of up to about 15 mm and allow for a protrusion of the jaw of up to about 15 mm. It will be appreciated that the lower AAD member 114 may extend any desirable distance. It is preferred to have the lower AAD member 114 extend downwardly and outwardly up to an amount such that it provides the most positive effect on opening and maintaining the patient's airway, without dislocating the patient's mandible.

As set forth above, the upper side of the lower plate 130, legs 120a, 120b and lips 122a and 122b preferably cooperate to form a guide to receive the upper plate 116. More specifically, when the AAD 110 is assembled, the upper plate 116 is received in the space between the bottom side of the lower plate 139, the legs 120a and 120b and the lips 122a and 122b. When the AAD is assembled, relative movement is allowed, when the ratchet mechanism does not prohibit it, between the lower plate 130 and the upper plate 116 in the longitudinal direction within the guide or space formed between the upper side of the lower plate 130, legs 120a, 120b and lips 122a and 122b.

The AAD 110 may further include an oxygen delivery housing and associated tubing of the type discussed above. The upper plate 116 may also include openings 162 therethrough in fluid communication with a space within an oxygen deliver housing, as described above. Further, a slot 163 may be provided to help secure the oxygen delivery housing. This allows fluid such as oxygen to be delivered through the opening 162 in the proximity of the patient's mouth, as described above. The opening 162 may be elongated to allow sufficient oxygen to be delivered to the patient. It will be appreciated that the opening 162 may take any suitable size and shape and may be located in any suitable location on the upper plate 16. Further, any number of openings 162 may be used.

The lower AAD component 114 may also include a guide generally indicated at 170. The guide 170 preferably depends from the lower plate 130. The guide 170 may include a first wall 172, and a pair of side walls 174. The side walls 174 extend transversely to the first wall 172 and from the edges thereof. The side walls 174 extend in the same direction from the first wall 172. The guide 170 may further include a projection 176 on each of the side walls 174. The projections 176 extend transversely to the side walls 174 and toward each other. As best seen in FIGS. 20-21, the first wall 172, side walls 174 and projections 176 define a channel 178. The first wall 172, side walls 174 and projections 176 therefore define the guide 170 that will receive a chin support slider member 186, as will be described below.

The guide 170 may include one or more slots 180. In the embodiment shown, the first wall 172 includes a pair of spaced slots 180, as best seen in FIGS. 15 and 20. A tab 182 depends from the first wall 172. The slots 180 allow the tab 182 to flex relative to the first wall 172. The tab 182 includes a pawl 185 thereon. The pawl preferably includes a flat surface and a ramped surface.

The lower AAD component 114 is preferably molded as a single piece. And as set forth above a relatively softer material such as urethane may be molded over, or otherwise placed over, the lower tooth guide 118. The lower AAD component 114 is preferably rigid. It will be appreciated, however that the legs 120a, 120b may flex slightly relative to the lower plate 130 when AAD is being assembled. Similarly, the tab 182 can flex relative to the first wall 172. Further, it will be appreciated that the lower AAD component may be made in any suitable manner, including in multiple pieces that are joined together.

The AAD 110 may further include a chin support generally indicated at 184. The chin support includes a slider member 186. The slider member 186 may have a generally rectangular cross section. The slider member 186 is disposed in the channel 178 defined by the guide 170. The slider member 186 can move or slide longitudinally within the channel 178.

The chin support 184 further includes a chin support platform 188. The chin support platform 188 extends transversely to the slider member 186 and outwardly from the channel 178 between the projections 176. The chin support platform 188 is connected to the slider member 186 and is preferably integrally formed therewith. In one embodiment, the chin support platform 188 is generally t-shaped having a larger oval area for contacting the patient's chin. It will be appreciated, however, that the chin support platform 188 may take any suitable geometric configuration. The chin support platform 188 may further include suitable support structure 190. The support structure may provide strength to the chin support platform 188. The chin support platform 188 may take any suitable geometric configuration. The chin support platform 188 may be engaged with a patient's chin, FIG. 22 to provide stability to the AAD 110.

As best seen in FIGS. 16 and 20, the slider member 186 may include a plurality of teeth 192 thereon. In one embodiment, the teeth 190 may extend from one side of the slider member 186. As best seen in FIG. 20, each of the teeth 190 has a ramped surface and a flat surface. The pawl 185 co-acts with the teeth 190 to provide a ratchet mechanism. The ratchet mechanism operates similar to the ratchet mechanism discussed above. The ratchet mechanism allows the slider member 186 to move upwardly as shown in FIG. 16 freely by allowing the ramped surfaces of the teeth 190 to move over the ramped surface of the pawl 185. This allows the tab 182 to flex as the slider member 186 is moved upwardly within the channel 178. After the ramped surface of the teeth 190 move over the ramped surface of the pawl 185, the flat surfaces of the respective tooth 190 and pawl 185 engage. This inhibits movement of the slider member 186 downwardly as viewed in FIG. 16 and away from the patient's chin. Because there are a plurality of teeth 190, the slider member 186 can move between a plurality of extended positions, spaced enough so that the chin support platform 188 will not contact a patient's chin, and a plurality of non-extended positions where the chin support platform 188 may contact a patient's chin.

The chin support 184 is preferably molded as a single piece. It is also preferred that the chin support 184 be made of a rigid material. It will be appreciated, however, that the chin support 184 may be made in any suitable manner, including in multiple pieces that are joined together.

To assemble the AAD 110, an oxygen delivery housing may first be secured to the upper plate 16 as described above. The upper AAD component 112 is positioned over the lower AAD component 114. The upper plate 116 may be aligned over the lower plate 130. The upper plate 116 and lower plate 130 are moved toward each other. The upper plate 116 may contact the ramped surfaces of the lips 122a and 122b on the legs 120a and 120b, respectively. As the upper plate 116 and lower plate 130 continue to move toward each other, the legs 120a and 120b flex outwardly relative to the axial direction of the upper plate 116. This allows the upper plate 116 to be positioned adjacent to the lower plate 130. Once the upper plate 116 has moved past the lips 122a, 122b, the legs 120a, 120b return to their unflexed position. In this position, the upper plate 116 is retained in the guide or space that is defined by the top side of the lower plate 130, legs 120a, 120b and lips 122a and 122b. The pawl 138 may engage one of the teeth 132 in the lower plate 130. It is preferred that when the AAD 110 is assembled, the upper tooth guide 118 and lower tooth guard 132 are positioned adjacent each other as best seen in FIG. 18. This may be referred to as the neutral or non-extended position.

The chin support 184 can then be connected. More particularly, the slider member 186 can be inserted into the channel 178 defined between the first wall 172, side walls 174 and projections 176. The slider member 186 can be inserted until the pawl 185 engages one of the teeth 192. It is preferred that the slider member 186 be inserted until it engages a tooth 192 in the upper portion of the slider member 186 when viewed in FIG. 20. In this way, the chin support 184 is in an extended position as best seen in FIG. 14. This allows for the maximum distance between the chin support platform 188 and the lower tooth guide 132. When the chin support 182 is in an extended position, it will be easier to position the AAD 110 relative to the patient. It will be appreciated that the chin support 184 may be positioned in the channel 178 prior to assembling the upper AAD and lower AAD components 112, 114, respectively.

In order to use the AAD 110 to open and maintain a patient's airway, the assembled AAD 110, having the upper AAD and lower AAD components 112, 114 in the neutral position and the, is positioned relative to a patient, as shown in FIG. 22. The upper tooth guide 118 is positioned to envelope a dentate or edentulous alveolar ridge of the patient. The lower tooth guide 132 is positioned in such a way the dental guard 134 extends to the lingual aspect of the patient's mandible. By using an upper tooth guide 118 and a lower tooth guide 132 as set forth, the AAD 110 can be used with a dentate or non-dentate application with a variety of dental arch shapes. It will be appreciated that in some instances it may be necessary to place the upper 116 and lower 130 plates of the AAD 110 in an extended position prior to positioning the AAD 110 relative to the patient. When the AAD 110 is first positioned relative to the patient, the chin support 184 is preferably in an extended position. The chin support 184 is then moved to a non-extended position by moving the chin support platform 188 until it engages the patient's chin, FIG. 22. The ratchet mechanism allows the slider member 186 and thereby the chin support platform 188 to move upwardly, as viewed in the Figures. The chin support platform 188 is moved until it engages the patient's chin with a desired amount of force. The ratchet mechanism inhibits the downward movement of the chin support platform 188, through the slider member 186 in a direction away from the patient's chin. More specifically, the flat surface of the pawl 185 engages the flat surface of the respective tooth 192 to inhibit movement of the slier member 186 in the downward direction. Positioning of the chin support platform 188 in this manner may help inhibit rotational or pivoting movement of the AAD 110 relative to the patient as the upper and lower plates 116, 130 are moved relative to each other. It is preferred that the chin support platform 188 engage the patient's chin, or lower jaw with sufficient force to inhibit rotational or pivoting movement of the AAD 11 and not so much force as to cause any damage to the patient.

Once the AAD 110 is positioned relative to the patient, the patient's mandible can be distracted and protruded as follows. A clinician, such as a surgeon, can place his thumbs on the distal surfaces of outermost sections 124a (those furthest away from the patient) of the upper force receiving plate 124. The clinician can place his index or other fingers on the back side (closest to the patient) of the lower force receiving plate 140. The clinician can hold his thumbs in the same position relative to the patient in such a way that the upper AAD component 112 remains in a relatively fixed position relative to the patient. The clinician can apply a force to the lower force receiving plate in a direction downwardly and away from the patient. By applying such a force, the lower AAD component 114 moves downwardly and away from the patient to an extended position, as best seen in FIG. 19. The ratchet mechanism, pawl 138 and teeth 136, allow movement of the lower AAD component 114 downwardly and outwardly away from the patient while inhibiting movement in the opposite direction. Because there are several teeth 136, the clinician can extend lower AAD component 114 to any desired extended position along the distraction path relative to the upper AAD component 112. This allows for relatively smooth mandibular distraction while minimizing any torque. This movement helps maintain an open airway for the patient. Further, the chin support 170 may help inhibit rotational or pivoting movement of the AAD 110 relative to the patient as the upper and lower plates 116, 130 are moved relative to each other.

Once the need for the AAD 110 ends, the upper 116 and lower 130 plates AAD 110 can be returned to the neutral position. This may be done by the clinician applying an upward force to the center section 124b of the upper force receiving plate 124. As best seen in FIGS. 15 and 16, the center section 124b can be raised sufficiently to raise the center section 128 of the upper plate 116 to disengage the pawl 138 from the teeth 136 of the lower plate 130. Once the pawl 138 is disengaged from the teeth 136, the lower AAD component 114 can return to the neutral position.

The chin support platform 188 is also moved to an extended position where it no longer engages a patient's chin. This may be done by the clinician applying a force to the tab 182 outwardly sufficiently to disengage the pawl 185 from the teeth 192. The clinician can then apply a force to the chin support platform 188 to move it, and the associated slider member 186 downwardly, as viewed in the Figures to a non-extended position. Upon returning the upper 116 and lower 130 plates of the AAD 110 to the neutral position and moving the chin support platform 188 to an extended position that is disengaged from the patient's chin, the clinician may then remove the AAD 110 from the patient.

The design of the AAD 10, 10', 110 may provide for a single use device which is relatively easy to use and provides simultaneous protrusion and distraction of the patient's jaw. The design also may also provide an oxygen delivery ability as well as or alternatively a carbon dioxide monitoring ability. Also, the design of the AAD may provide an AAD that is atraumatic to the nasal cavity or the oral cavity.

The embodiments have been described in an illustrative manner. It is to be understood that the terminology which has been used is intended to be in the nature of words of description, rather than of limitation. Obviously, many modifications and variations are possible in light of the above teachings. By way of non-limiting example, where components are described as being molded as a single piece, they may be fabricated independently and joined together. Similarly, various features among the several embodiments may be incorporated into other embodiments even though they might not be specifically shown in the drawings. Additionally while one specific type of ratchet mechanism is described, it will be appreciated that a suitable configuration that allows for movement in one direction while prohibiting movement in the opposite direction is within the scope of the described embodiments. Further, the pawls and teeth described may be reversed in that, for example the pawl 84 may be on the lower AAD component 114 and the teeth on the Upper AAD component 112. It is therefore, to be understood that invention is defined by the appended claims.

What is claimed is:
1. An airway assist device comprising:
a first airway assist device component including an upper plate and an upper tooth guide connected to the upper plate, the upper plate including a first portion and a descending portion connected to the first portion and extending at an angle relative to the first portion;
a second airway assist device component including a lower plate and a lower tooth guide connected to the lower plate, the lower plate including a first portion and a descending portion connected to the first portion and extending at an angle relative to the first portion;

the first airway assist device component connected with the second airway assist device component to allow relative movement between the first and second airway assist device components between a neutral position and at least one extended position; and a ratchet mechanism acting between the first and second first airway assist device components, the ratchet mechanism acting between the upper and lower plates to allow for movement of the second first airway assist device component from the neutral position to an extended position and inhibiting movement of the first airway assist device component from an extended position toward the neutral position.

2. An airway assist device as set forth in claim 1 further comprising a chin guide comprising a slider member and a chin support connected to the slider member, moveable between at least one extended position and at least one non-extended position.

3. An airway assist device as set forth in claim 2 wherein the chin guide further comprises a first wall, the slider member moveable relative to the first wall, and a second ratchet mechanism acting between the first wall and the slider member, the second ratchet mechanism to allow for movement of the slider member from an extended position to a non-extended position and inhibit movement of the slider member from a non-extended position to an extended position.

4. The airway assist device as set forth in claim 3 wherein the ratchet mechanism comprises a pawl on one of the upper plate or lower plate and a plurality of teeth on the other of the upper plate or lower plate, the pawl being selectively engagable with the teeth.

5. The airway assist device as set forth in claim 4 wherein the upper plate includes a center portion and at least one outer portion, the center portion being moveable with respect to the outer portion, the center portion including the pawl thereon, and the lower plate including the plurality of teeth thereon.

6. An airway assist device as set forth in claim 4 wherein the first wall includes a tab having a pawl thereon and the slider member having a plurality of teeth thereon, the pawl co-acting with the teeth to allow for movement of the slider member from an extended position to a non-extended position and inhibit movement of the slider member from a non-extended position to an extended position, the tab being moveable to disengage the pawl from the teeth to allow for movement of the slider member from a non-extended position to an extended position.

7. An airway assist device as set forth in claim 5 wherein the upper plate includes a force receiving member extending transversely thereto and the lower plate includes a force receiving member extending transversely thereto.

8. An airway assist device as set forth in claim 4 wherein the first portion of the upper plate and the descending portion of the upper plate form an angle of between about 120 and 165 degrees therebetween.

9. An airway assist device as set forth in claim 4 wherein the first portion of the lower plate and the descending portion of the lower plate form an angle of between about 120 and 165 degrees therebetween.

10. An airway assist device as set forth in claim 4 further comprising at least one hard stop.

11. An airway assist device as set forth in claim 4 further comprising an oxygen delivery housing comprising an enclosure wall connected to the upper plate to form a space between the enclosure wall and the upper plate.

12. An airway assist device as set forth in claim 11 wherein the oxygen delivery housing further comprises a tubing connecting portion defining a fluid passageway.

13. An airway assist device as set forth in claim 12 wherein the upper plate includes at least one opening in fluid communication with space between the enclosure wall and the upper plate.

14. An airway assist device as set forth in claim 13 wherein the oxygen delivery housing comprises an enclosure wall and a septum connected to the upper plate to form a plurality of spaces between the enclosure wall and the upper plate.

15. An airway assist device as set forth in claim 14 wherein the oxygen delivery housing further comprises at least one tubing connecting portion defining a fluid passageway with each of the plurality of spaces.

16. An airway assist device as set forth in claim 15 wherein the upper plate includes at least one opening in fluid communication with each of the plurality of spaces between the enclosure wall and the upper plate.

17. An airway assist device comprising:

a first airway assist device component including an upper plate and an upper tooth guide connected to the upper plate, the upper plate including a first portion and a descending portion connected to the first portion and extending at an angle relative to the first portion;

a second airway assist device component including a lower plate and a lower tooth guide connected to the lower plate, the lower plate including a first portion and a descending portion connected to the first portion and extending at an angle relative to the first portion;

the first airway assist device component connected with the second airway assist device component to allow relative movement between the first and second airway assist device components between a neutral position and at least one extended position;

a ratchet mechanism acting between the first and second first airway assist device components, the ratchet mechanism acting between the upper and lower plates to allow for movement of the second first airway assist device component from the neutral position to an extended position and inhibiting movement of the first airway assist device component from an extended position toward the neutral position;

a chin guide comprising a slider member, a first wall and a chin support connected to the slider member, the slider member moveable relative to the first wall between at least one extended position and at least one non-extended position; and a second ratchet mechanism acting between the first wall and the slider member, the second ratchet mechanism to allow for movement of the slider member from an extended position to a non-extended position and inhibit movement of the slider member from a non-extended position to an extended position.

18. The airway assist device as set forth in claim 17 wherein the ratchet mechanism comprises a pawl on one of the upper plate or lower plate and a plurality of teeth on the other of the upper plate or lower plate, the pawl being selectively engagable with the teeth.

19. A method of maintaining airway patency comprising:

position an upper tooth guide of a first airway assist device component relative to a patient and positioning a lower tooth guide of a second airway assist device component relative to a patient;

positioning a chin support against the patient's chin and maintaining the chin support in position by a ratchet mechanism;

applying a force to the second airway assist device component in a direction downwardly and away from the patient to protrude and distract the patient's mandible; and maintaining the second airway assist device component in an extended position by a ratchet mechanism.

20. A method of maintaining an airway as set forth in claim 19 further comprising supplying oxygen to the patient through the first airway assist device component and monitoring the patient's end-tidal carbon dioxide wave form and respiratory rate.

\* \* \* \* \*